United States Patent
Haaning et al.

(10) Patent No.: US 9,353,365 B2
(45) Date of Patent: *May 31, 2016

(54) FACTOR VII OR VIIA POLYPEPTIDE VARIANTS

(75) Inventors: Jesper Mortensen Haaning, Redwood City, CA (US); Kim Vilbour Andersen, Broenshoej (DK)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/707,453

(22) Filed: Feb. 17, 2010

(65) Prior Publication Data

US 2010/0260741 A1    Oct. 14, 2010

Related U.S. Application Data

(63) Continuation of application No. 10/512,754, filed as application No. PCT/DK03/00267 on Apr. 29, 2003, now Pat. No. 7,700,733.

(60) Provisional application No. 60/376,679, filed on Apr. 30, 2002.

(51) Int. Cl.
*A61K 38/00* (2006.01)
*C12N 9/64* (2006.01)

(52) U.S. Cl.
CPC ....... *C12N 9/6437* (2013.01); *C12Y 304/21021* (2013.01); *A61K 38/00* (2013.01)

(58) Field of Classification Search
None
See application file for complete search history.

(56) References Cited

U.S. PATENT DOCUMENTS 6,806,063 B2 * 10/2004 Pedersen et al. ............. 435/69.1
7,700,733 B2 * 4/2010 Haaning et al. ............... 530/381

OTHER PUBLICATIONS

Medzihradsky et al. (Anal. Chem., 1997, vol. 69, pp. 3986-3994).*

* cited by examiner

*Primary Examiner* — Hope Robinson
(74) *Attorney, Agent, or Firm* — Bayer Healthcare LLC

(57) ABSTRACT

The present invention relates to novel polypeptide variants of factor VII (FVII) or factor VIIa (FVIIa) polypeptides, where said variants comprise an amino acid substitution in position 10 and 32 and where said variants further comprise a sugar moiety covalently attached to an introduced in vivo N-glycosylation site located outside of the Gla domain. Such polypeptide variants are useful in therapy, in particular for the treatment of a variety of coagulation-related disorders, such as trauma.

21 Claims, No Drawings

FACTOR VII OR VIIA POLYPEPTIDE VARIANTS

FIELD OF THE INVENTION

The present invention relates to novel polypeptide variants of factor VII (FVII) or factor VIIa (FVIIa) polypeptides, where said variants comprise an amino acid substitution in position 10 and 32 and where said variants further comprise a sugar moiety covalently attached to an introduced in vivo N-glycosylation site.

The present invention also relates to use of such polypeptide variants in therapy, in particular for the treatment of a variety of coagulation-related disorders.

BACKGROUND OF THE INVENTION

Blood coagulation is a process consisting of a complex interaction of various blood components (or factors) that eventually results in a fibrin clot. Generally, the blood components participating in what has been referred to as the "coagulation cascade" are proenzymes or zymogens, i.e. enzymatically inactive proteins that are converted into an active form by the action of an activator. One of these coagulation factors is FVII.

FVII is a vitamin K-dependent plasma protein synthesized in the liver and secreted into the blood as a single-chain glycoprotein with a molecular weight of 53 kDa (Broze & Majerus, J. Biol. Chem. 1980; 255:1242-1247). The FVII zymogen is converted into an activated form (FVIIa) by proteolytic cleavage at a single site, R152-I153, resulting in two chains linked by a single disulfide bridge. FVIIa in complex with tissue factor (FVIIa complex) is able to convert both factor IX and factor X into their activated forms, followed by reactions leading to rapid thrombin production and fibrin formation (Østerud & Rapaport, Proc Natl. Acad Sci USA 1977; 74:5260-5264).

FVII undergoes post-translational modifications, including vitamin K-dependent carboxylation resulting in ten γ-carboxyglutamic acid residues in the N-terminal region of the molecule. Thus, residue number 6, 7, 14, 16, 19, 20, 25, 26, 29 and 35 shown in SEQ ID NO:2 are γ-carboxyglutamic acids residues in the Gla domain important for FVII activity. Other post-translational modifications include sugar moiety attachment at two naturally occurring N-glycosylation sites at position 145 and 322, respectively, and at two naturally occurring O-glycosylation sites at position 52 and 60, respectively.

The gene coding for human FVII (hFVII) has been mapped to chromosome 13 at q34-qtr 9 (de Grouchy et al., Hum Genet. 1984; 66:230-233). It contains nine exons and spans 12.8 Kb (O'Hara et al., Proc Natl Acad Sci USA 1987; 84:5158-5162). The gene organisation and protein structure of FVII are similar to those of other vitamin K-dependent procoagulant proteins, with exons 1a and 1b encoding for signal sequence; exon 2 the propeptide and Gla domain; exon 3 a short hydrophobic region; exons 4 and 5 the epidermal growth factor-like domains; and exon 6 through 8 the serine protease catalytic domain (Yoshitake et al., Biochemistry 1985; 24: 3736-3750).

Reports exist on experimental three-dimensional structures of hFVIIa (Pike et al., PNAS. U.S.A., 1999; 96:8925-30 and Kemball-Cook et al., J. Struct. Biol, 1999; 127:213-223); of hFVIIa in complex with soluble tissue factor using X-ray crystallographic methods (Banner to et al., Nature, 1996; 380:41 and Zhang et al., J. Mol. Biol, 1999; 285: 2089); and of smaller fragments of hFVII (Muranyi et al., Biochemistry, 1998; 37:10605 and Kao et al., Bio-chemistry, 1999; 38:7097).

Some protein-engineered variants of FVII have been reported. See, e.g., Dickinson & Rut; J Bio Chem, 1997; 272:19875-19879, Kemball-Cook et al., J Biol Chem, 1998; 273:8516-8521, Bharadwaj et al., J Biol Chem, 1996; 271: 30685-30691, Ruf et al., Biochemistry, 1999; 38:1957-1966; WO 99/20767; WO 00/11416; WO 02/22776; WO 02/38162; WO 01/83725; WO 01/58935; U.S. Pat. No. 5,580,560.

Reports exist on expression of FVII in BHK or other mammalian cells (WO 92/15686, WO 91/11514 and WO 88/10295) and co-expression of FVII and kex2 endoprotease in eukaryotic cells (WO 00/28065).

Commercial preparations of human recombinant FVIIa are sold as NovoSeven®. NovoSeven® is indicated for the treatment of bleeding episodes in hemophilia A or B patients. NovoSeven® is the only rhFVIIa for effective and reliable treatment of bleeding episodes available on the market.

An inactive form of FVII in which arginine 152 and/or isoleucine 153 is/are modified has been reported in WO91/1154. These amino acids are located at the activation site. WO 96/12800 describes inactivation of FVIIa by a serine proteinase inhibitor; inactivation by carbamylation of FVIIa at the α-amino acid group I153 has been described by Petersen et al., Eur J Biochem, 1999; 261:124-129. The inactivated form is capable of competing with wild-type FVII or FVIIa for binding to tissue factor and inhibiting clotting activity. The inactivated form of FVIIa is suggested to be used for treatment of patients being in hypercoagulable states, such as patients with sepsis, in risk of myocardial infarction or of thrombotic stroke.

A circulating rhFVIIa half-life of 2.3 hours was reported in "Summary Basis for Approval for NovoSeven®", FDA reference number 96-0597. Relatively high doses and frequent administration are necessary to reach and sustain the desired therapeutic or prophylactic effect. As a consequence adequate dose regulation is difficult to obtain and the need of frequent intravenous administrations imposes restrictions on the patient's way of living.

In connection with treatment of uncontrolled bleedings, such as trauma, it is believed that factor VIIa is capable of activating factor X to factor Xa without binding to tissue factor, and this activation reaction is believed to occur primarily on activated blood platelets (Hedner et al. Blood Coagulation & Fibrinolysis, 2000; 11; 107-111). However, hFVIIa or rhFVIIa has a to low activity towards factor X in the absence of tissue factor and, consequently, treatment of uncontrolled bleeding, for example in trauma patients, requires relatively high and multiple doses of hFVIIa or rhFVIIa. Therefore, in order to treat uncontrolled bleedings more efficiently (to minimize blood loss) there is need for improved FVIIa molecules, which possess a high activity toward factor X in the absence of tissue factor. Such improved FVIIa molecules will exhibit a lowered clotting time (or faster action) as compared to rhFVIIa when administered in connection with uncontrolled bleedings.

A molecule with a longer circulation half-life would decrease the number of necessary administrations. Given the association of current the rhFVIIa product with frequent injections, and the potential for obtaining more optimal therapeutic FVIIa levels with concomitant enhanced therapeutic effect, there is a clear need for improved FVII- or FVIIa-like molecules.

One way to increase the circulation half-life of a protein is to ensure that renal clearance of the protein is reduced. This may be achieved by conjugating the protein to a chemical moiety, which is capable of conferring reduced renal clearance to the protein.

Furthermore, attachment of a chemical moiety to the protein or substitution of amino acids exposed to proteolysis may effectively block a proteolytic enzyme from contact leading to proteolytic degradation of the protein, Polyethylene glycol (PEG) is one such chemical moiety that has been used in the preparation of therapeutic protein products. WO 98/32466 suggests that FVII, among many other proteins, may be PEGylated but does not contain any further information in this respect WO 01/58935 discloses a new strategy for developing FVII or FVIIa molecules having inter alia an increased half-life.

As indicated above, another problem in current rhFVIIa treatment is the relative instability of the molecule with respect to proteolytic degradation. Proteolytic degradation is a major obstacle for obtaining a preparation in solution as opposed to a lyophilized product. The advantage of obtaining a stable soluble preparation lies in easier handling for the patient, and, in the case of emergencies, quicker action, which potentially can become life saving. Attempts to prevent proteolytic degradation by site directed mutagenesis at major proteolytic sites have been disclosed in WO 88/10295.

One object of the present invention is to provide improved FVII or FVIIa molecules (FVII or FVIIa variants) with a longer circulation half-life (thereby decreasing the number of necessary administrations) and which are capable of activating factor X to factor Xa (without binding to tissue factor) more efficiently than hFVIIa or rhFVIIa (thereby being able to treat uncontrolled bleedings, such as a trauma, more efficiently).

Another object of the present invention is to provide improved FVII or FVII molecules (FVII or FVIIa variants) with an increased bioavailability (such as an increased Area Under the Curve as compared to rhFVIIa when administered intravenously) and which are capable of activating factor X to factor Xa (without binding to tissue factor) more efficiently than hFVIIa or rhFVIIa (thereby being able to treat uncontrolled bleedings, such as a trauma, more efficiently).

These objects are met by the FVII or FVIIa variants provided herein.

BRIEF DISCLOSURE OF THE INVENTION

In its broadest aspect the present invention relates to a FVII or FVIIa polypeptide variant having an amino acid sequence comprising 3-15 amino acid modifications relative to hFVII or hFVIIa having the amino acid sequence shown in SEQ ID NO:2, wherein said amino acid sequence of the variant comprises an amino acid substitution in position 10 and 32 and wherein a sugar moiety is covalently attached to an introduced in vivo N-glycosylation site located outside the Gla domain.

Another aspect of the invention relates to a nucleotide sequence encoding the polypeptide variant of the invention.

In a further aspect the invention relates to an expression vector comprising the nucleotide sequence of the invention.

In a still further aspect the invention relates to a host cell comprising the nucleotide sequence of the invention or the expression vector of the invention.

In an even further aspect the invention relates to a pharmaceutical composition comprising the polypeptide variant of the invention, and a pharmaceutical acceptable carrier or excipient.

Still another aspect of the invention relates to the polypeptide variant of the invention, or the pharmaceutical composition of the invention, for use as a medicament.

Further aspects of the present invention will be apparent from the below description as well as from the appended claims.

DETAILED DISCLOSURE OF THE INVENTION

Definitions

In the context of the present application and invention the following definitions apply:

The term "conjugate" (or interchangeably "conjugated polypeptide") is intended to indicate a heterogeneous (in the sense of composite or chimeric) molecule formed by the to covalent attachment of one or more polypeptide(s) to one or more non-polypeptide moieties such as polymer molecules, lipophilic compounds, sugar moieties or organic derivatizing agents. Preferably, the conjugate is soluble at relevant concentrations and conditions, i.e. soluble in physiological fluids such as blood. Examples of conjugated polypeptides of the invention include glycosylated and/or PEGylated polypeptides.

The term "covalent attachment" or "covalently attached" means that the polypeptide variant and the non-polypeptide moiety are either directly covalently joined to one another, or else are indirectly covalently joined to one another through an intervening moiety or moieties, such as a bridge, spacer, or linkage moiety or moieties.

The term "non-polypeptide moiety" is intended to mean a molecule, different from a as peptide polymer composed of amino acid monomers and linked together by peptide bonds, which molecule is capable of conjugating to an attachment group of the polypeptide variant of the invention. Preferred examples of such molecules include polymer molecules, sugar moieties, lipophilic compounds or organic derivatizing agents. When used in the context of a conjugated variant of the invention it will be understood that the non-polypeptide moiety is linked to the polypeptide part of the conjugated variant through an attachment group of the polypeptide. As explained above, the non-polypeptide moiety can be directly covalently joined to the attachment group or it can be indirectly covalently joined to the attachment group through an intervening moiety or moieties, such as a bridge spacer or linker moiety or moieties.

A "polymer molecule" is a molecule formed by covalent linkage of two or more monomers, wherein none of the monomers is an amino acid residue, except where the polymer is human albumin or another abundant plasma protein. The term "polymer" may be used interchangeably with the term "polymer molecule". The term is also intended to cover carbohydrate molecules attached by in vitro glycosylation, i.e. a synthetic glycosylation performed in vitro normally involving covalently linking a carbohydrate molecule to an attachment group of the polypeptide variant, optionally using a crosslinking agent. In vitro glycosylation is discussed in detail further below.

The term "sugar moiety" is intended to indicate a carbohydrate-containing molecule comprising one or more monosaccharide residues, capable of being attached to the polypeptide variant (to produce a polypeptide variant conjugate in the form of a glycosylated polypeptide variant) by way of in vivo glycosylation. The term "in vivo glycosylation" is intended to mean any attachment of a sugar moiety occurring in vivo, i.e. during posttranslational processing in a glycosylating cell used for expression of the polypeptide variant, e.g. by way of N-linked and O-linked glycosylation. The exact oligosaccharide structure depends, to a large extent, on the glycosylating organism in question.

An "N-glycosylation site" has the sequence N-X-S/T/C, wherein X is any amino acid residue except proline, N is asparagine and S/T/C is either serine, threonine or cysteine, preferably serine or threonine, and most preferably threonine. Preferably, the amino acid residue in position +3 relative to the asparagines residue is not a proline residue.

An "O-glycosylation site" is the OH-group of a serine or threonine residue.

The term "attachment group" is intended to indicate a functional group of the polypeptide variant, in particular of an amino acid residue thereof or a carbohydrate moiety, capable of attaching a non-polypeptide moiety such as a polymer molecule, a lipophilic molecule, a sugar moiety or an organic derivatizing agent. Useful attachment groups and their matching non-polypeptide moieties are apparent from the table below.

most preferably threonine). Although the asparagine residue of the N-glycosylation site is the one to which the sugar moiety is attached during glycosylation, such attachment cannot be achieved unless the other amino acid residues of the N-glycosylation site is present.

Accordingly, when the non-polypeptide moiety is a sugar moiety and the conjugation is to be achieved by in vivo N-glycosylation, the term "amino acid residue comprising an attachment group for a non-polypeptide moiety" as used in connection with alterations of the amino acid sequence of the polypeptide is to be understood as meaning that one or more amino acid residues constituting an in vivo N-glycosylation site are to be altered in such a manner that a functional in vivo N-glycosylation site is introduced into the amino acid sequence.

In the present application, amino acid names and atom names (e.g. CA, CB, CD, CG, SG, NZ, N, O, C, etc) are used as defined by the Protein DataBank (PDB) based on the

| Attachment group | Amino acid | Examples of non-polypeptide moiety | Conjugation method/-Activated PEG | Reference |
|---|---|---|---|---|
| —NH$_2$ | N-terminal, Lys | Polymer, e.g. PEG, with amide or imine group | mPEG-SPA Tresylated mPEG | Shearwater Inc. Delgado et al, critical reviews in Therapeutic Drug Carrier Systems 9(3, 4): 249-304 (1992) |
| —COOH | C-terminal, Asp, Glu | Polymer, e.g. PEG, with ester or amide group Carbohydrate moiety | mPEG-Hz In vitro coupling | Shearwater Inc |
| —SH | Cys | Polymer, e.g. PEG, with disulfide, maleimide or vinyl sulfone group Carbohydrate moiety | PEG-vinylsulphone PEG-maleimide In vitro coupling | Shearwater Inc Delgado et al, critical reviews in Therapeutic Drug Carrier Systems 9(3, 4): 249-304 (1992) |
| —OH | Ser, Thr, Lys, OH— | Sugar moiety PEG with ester, ether, carbamate, carbonate | In vivo O-linked glycosylation | |
| —CONH$_2$ | Asn as part of an N-glycosylation site | Sugar moiety Polymer, e.g. PEG | In vivo N-glycosylation | |
| Aromatic residue | Phe, Tyr, Trp | Carbohydrate moiety | In vitro coupling | |
| —CONH$_2$ | Gln | Carbohydrate moiety | In vitro coupling | Yan and Wold, Biochemistry, 1984, Jul. 31; 23(16): 3759-65 |
| Aldehyde Ketone | Oxidized oligsaccharide | Polymer, e.g. PEG, PEG-hydrazide | PEGylation | Andresz et al., 1978, Makromol. Chem. 179: 301; WO 92/16555, WO 00/23114 |
| Guanidino | Arg | Carbohydrate moiety | In vitro coupling | Lundblad and Noyes, Chimical Reagents for Protein Modification, CRC Press Inc., Florida, USA |
| Imidazole ring | His | Carbohydrate moiety | In vitro coupling | As for guanidine |

For in vivo N-glycosylation, the term "attachment group" is used in an unconventional way to indicate the amino acid residues constituting a N-glycosylation site (with the sequence N-X-S/T/C, wherein X is any amino acid residue except proline, N is asparagine and S/T/C is either serine, threonine or cysteine, preferably serine or threonine, and IUPAC nomenclature (IUPAC Nomenclature and Symbolism for Amino Acids and Peptides (residue names, atom names, etc.), *Eur. J. Biochem.*, 138, 9-37 (1984) together with their corrections in *Eur. J. Biochme.*, 152, 1 (1985)).

The term "amino acid residue" is intended to indicate an amino acid residue contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues.

The terminology used for identifying amino acid positions is illustrated as follows: I205 indicates that position 205 is occupied by an isoleucine residue in the amino acid sequence shown in SEQ ID NO:2. I205T indicates that the isoleucine residue of position 205 has been substituted with a threonine residue. Alternative substitutions are indicated with a "/", e.g. I205S/T means an amino acid sequence in which isoleucine in position 205 is substituted with either serine or threonine. Multiple substitutions are indicated with a "+", e.g. K143N+N145T means a substitution of the lysine residue in position 143 with an asparagine residue and a substitution of the asparagine residue in position 145 with a threonine residue. Insertion of an additional amino acid residue is indicated in the following way: Insertion of a tyrosine residue to after A3 (i.e. in position 4) is indicated by A3AY (leading to insertion of a tyrosine residue in position 4). A deletion of an amino acid residue is indicated by an asterix. For example, deletion of a valine residue in position 172 is indicated by V172*. Simultaneous insertion and substitution are indicated in the following way: Substitution of an alanine residue in position 175 with a threonine residue followed by insertion of a leucine residue after position 175 is indicated A175TL.

Unless otherwise indicated, the numbering of amino acid residues made herein is made relative to the amino acid sequence of the hFVII/hFVIIa polypeptide (SEQ ID 140:2).

The term "differs from" as used in connection with specific mutations is intended to allow for additional differences being present apart from the specified amino acid difference. For instance, in addition to the introduction of in vivo N-glycosylation sites (located outside the Gla domain), the polypeptide may comprise other modifications that are not related to introduction of such amino acid residues. In a similar way, in addition to the modifications performed in the Gla domain aiming at increasing the phospholipid membrane binding affinity, the polypeptide may contain other modifications that are not necessarily related to this effect. Thus, in addition to the amino acid modifications disclosed herein, it will be understood that the amino acid sequence of the polypeptide variant of the invention may, if desired, contain other alterations, i.e. other substitutions, insertions or deletions. These may, for example, include truncation of the N- and/or C-terminus by one or more amino acid residues (e.g. by 1-10 amino acid residues), or addition of one or more extra residues at the N- and/or C-terminus, e.g. addition of a methionine residue at the N-terminus or introduction of a cysteine residue near or at the C-terminus, as well as "conservative amino acid substitutions", i.e. substitutions performed within groups of amino acids with similar characteristics, e.g. small amino acids, acidic amino acids, polar amino acids, basic amino acids, hydrophobic amino acids and aromatic amino acids.

Examples of such conservative substitutions are shown in the below table.

| 1 | Alanine (A) | Glycine (G) | Serine (S) | Threonine (T) |
|---|---|---|---|---|
| 2 | Aspartic acid (D) | Glutamic acid (E) | | |
| 3 | Asparagine (N) | Glutamine (Q) | | |
| 4 | Arginine (R) | Histidine (H) | Lysine (K) | |
| 5 | Isoleucine (I) | Leucine (L) | Methionine (M) | Valine (V) |
| 6 | Phenylalanine (F) | Tyrosine (Y) | Tryptophan (W) | |

Still other examples of additional modifications are disclosed in the section entitled "Other modifications outside the Gla domain" below.

The term "nucleotide sequence" is intended to indicate a consecutive stretch of two or more nucleotide molecules. The nucleotide sequence may be of genomic, cDNA, RNA, semi-synthetic, synthetic origin, or any combinations thereof.

The term "polymerase chain reaction" or "PCR" generally refers to a method for amplification of a desired nucleotide sequence in vitro, as described, for example, in U.S. Pat. No. 4,683,195. In general, the PCR method involves repeated cycles of primer extension synthesis, using oligonucleotide primers capable of hybridising preferentially to a template nucleic acid.

The term "vector" refers to a plasmid or other nucleotide sequences that are capable of replicating within a host cell or being integrated into the host cell genome, and as suck, are useful for performing different functions in conjunction with compatible host cells (a vector-host system): to facilitate the cloning of the nucleotide sequence, i.e. to produce usable quantities of the sequence, to direct the expression of the gene product encoded by the sequence and to integrate the nucleotide sequence into the genome of the host cell. The vector will contain different components depending upon the function it is to perform.

"Cell", "host cell", "cell line" and "cell culture" are used interchangeably herein and all such terms should be understood to include progeny resulting from growth or culturing of a cell.

"Transformation" and "transfection" are used interchangeably to refer to the process of introducing DNA into a cell.

"Operably linked" refers to the covalent joining of two or more nucleotide sequences, by means of enzymatic ligation or otherwise, in a configuration relative to one another such that the normal function of the sequences can be performed. For example, the nucleotide sequence encoding a presequence or secretory leader is operably linked to a nucleotide sequence coding for a polypeptide if it is expressed as a preprotein that participates in the secretion of the polypeptide: a promoter or enhancer is operably linked to a coding sequence if it affects the transcription of the sequence; a ribosome binding site is operably linked to a coding sequence if it is positioned so as to facilitate translation. Generally, "operably linked" means that the nucleotide sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

In the context of the present invention the terms "modification" or "amino acid to modification" is intended to cover replacement of an amino acid side chain, substitution of an amino acid residue, deletion of an amino acid residue and/or insertion of an amino acid residue.

The terms "mutation" and "substitution" are used interchangeably herein.

The term "introduce" refers to introduction of an amino acid residue by substitution of an existing amino acid residue or, alternatively, by insertion of an additional amino acid residue.

The term "remove" refers to removal of an amino acid residue by substitution of the amino acid residue to be removed by another amino acid residue or, alternatively, by deletion (without substitution) of the amino acid residue to be removed The term "FVII" or "FVII polypeptide" refers to a FVII molecule provided in single chain form. One example of a FVII polypeptide is wild-type human FVII (hFVII) shown in SEQ ID NO:2. It should be understood, however, that the term "FVII polypeptide" also covers hFVII-like molecules, such as fragments or variants of SEQ ID NO:2, in particular variants where the sequence comprises at least one, such as 1-15, e.g., 1-10, amino acid modifications as compared to SEQ ID NO:2.

The term "FVIIa" or "FVIIa polypeptide" refers to a FVIIa molecule provided in its activated two-chain form. When the amino acid sequence of SEQ ID NO:2 is used to describe the amino acid sequence of FVIIa it will be understood that the peptide bond between R152 and I153 of the single-chain form has been cleaved, and that one of the chains comprises amino acid residues 1-152, the other chain amino acid residues 153-406. The terms "rFVII" and "rFVIIa" refer to FVII and FVIIa polypeptides produced by recombinant techniques.

The terms "hFVII" and "hFVIIa" refer to human wild-type FVII and FVIIa, respectively, having the amino acid sequence shown in SEQ ID NO:2

The terms "rhFVII" and "rhFVIIa" refer to human wild-type FVII and FVIIa, having the amino acid sequence shown in SEQ ID NO:2, produced by recombinant means. An example of rhFVIIa is NovoSeven®.

When used herein, the term "Gla domain" is intended to cover amino acid residues no. 1 to 45 of SEQ ID NO:2.

Accordingly, the term "located outside the Gla domain" covers amino acid residue no. 46-406 of SEQ ID NO:2.

The abbreviations "TF" and "TFPI" mean Tissue Factor and Tissue Factor Pathway Inhibitor, respectively.

The term "protease domain" is used about residues 153-406 counted from the N-terminus.

The term "catalytic site" is used to mean the catalytic triad consisting of S344, D242 and H193 of the polypeptide variant.

The term "parent" is intended to indicate the molecule to be modified/improved in accordance with the present invention. Although the parent polypeptide to be modified by the present invention may be any FVII or FVIIa polypeptide, and thus be derived from any origin, e.g. a non-human mammalian origin, it is preferred that the parent polypeptide is hFVII or hFVIIa A "variant" is a polypeptide, which differs in one or more amino acid residues from its parent polypeptide, normally in 3-15 amino acid residues (e.g. in 3, 4, 5, 6, 7, 8, 9, 10, 11, 12, 13, 14 or 15 amino acid residues), such as in 3-10 amino acid residues, e.g. in 3-8 or 3-5 amino acid residues. In other words, a "variant" typically contains 3-15 amino acid modifications (for example 3, 4, 5, 6, 7, 8, 9, 10, 11, 12, 13, 14 or 15 amino acid modifications), such as 3-10 amino acid modifications, e.g. 3-8 or 3-5 amino acid modifications relative to the parent polypeptide. In the present context, the term "modification" encompasses insertions, deletions, substitutions and combinations thereof. It will be understood that a polypeptide variant according to the present invention will be modified in at least three positions, namely in at least position 10 and 32 (located in the Gla domain) and in at least one position located outside the Gla domain, where said at least one modification creates an in vivo N-glycosylation site.

The term "clotting activity" is used to mean the activity measured in the "Clotting Assay" described herein. In order to exhibit "clotting activity" a variant of the invention, in its activated form, should have at least 10% of the clotting activity of rhFVIIa when assayed in the "Clotting Assay" described herein. In a preferred embodiment of the invention the variant, in its activated form, has at least 20% of the clotting activity of rhFVIIa, such as at least 30%, e.g. at least 40%, more preferably at least 50%, such as at least 60%, e.g. at least 70%, even more preferably at least 80%, such as at least 90% of the clotting activity of rhFVIIa when assayed in the "Clotting Assay" described herein. In an interesting embodiment the variant, in its activated form, has substantially the same clotting activity as rhFVIIs, such as a clotting activity of 75-125% of the clotting activity of rhFVIIa.

The term "amidolytic activity" is used to mean the activity measured in the "Amidolytic Assay" described herein. In order to exhibit "amidolytic activity" a variant of the invention, in its activated form, should have at least 10% of the amidolytic activity of rhFVIIa when assayed in the "Amidolytic Assay" described herein. In a preferred embodiment of the to invention the variant, in its activated form, has at least 20% of the amidolytic activity of rhFVIIa, such as at least 30%, e.g. at least 40%, more preferably at least 50%, such as at least 60%, e.g. at least 70%, even more preferably at least 80%, such as at least 90% of the amidolytic activity of rhFVIIa when assayed in the "Amidolytic Assay" described herein. In an interesting embodiment the variant, in its activated form, has substantially the same amidolytic activity as rhFVIIs, such as an amidolytic activity of 75-125% of the amidolytic activity of rhFVIIa.

In the present context, the term "activity" is also used in connection with the variants capability of activating FX to FXa. This activity is also denoted "FX activation activity" or "FXa generation activity".

The term "increased FX activation activity" or "increased FXa generation activity" is used to indicate that a variant of the invention, in its activated form, has a statistically significantly increased capability to activate FX to FXa as compared to rhFVIIa or. To what extent a variant of the invention (in its activated form) has an increased FX activation activity may conveniently be determined in the "TF-independent Factor X Activation Assay" described herein.

The term "stronger clot" or "increased clot strength" is used to indicate that the strength of the clot generated by the polypeptide variant is statistically significantly increased relative to that generated by rhFVIIa as determined under comparable conditions. This effect may be determined as the Area Under the Curve ($AUC_{throm}$) generated by the variant of the invention, in its activated form, when assayed in the "Thrombogram Assay" disclosed herein. In a similar way, the term "increased $AUC_{throm}$" is used to indicate that the Area Under the Curve generated by the variant (in its activated form) is statistically significantly increased relative to that generated by rhFVIIa as determined under comparable conditions and when, measured in the "Thrombogram Assay" described herein The term "$T_{max}$" is used about the time it takes to obtain the maximum thrombin activity level in the "Thrombogram Assay".

The term "immunogenicity" as used in connection with a given substance is intended to indicate the ability of the substance to induce a response from the immune system. The immune response may be a cell, or antibody mediated response (see, e.g., Roitt: Essential Immunology (8th Edition, Blackwell) for further definition of immunogenicity). Normally, reduced antibody reactivity will be an indication of reduced immunogenicity. The reduced immunogenicity may be determined by use of any suitable method known in the art, e.g. in vivo or in vitro.

The term "functional in vivo half-life" is used in its normal meaning, i.e. the time at which 50% of the biological activity of the polypeptide is still present in the body/target organ, or the time at which the activity of the polypeptide is 50% of the initial value.

As an alternative to determining functional in vivo half-life, "serum half-life" may be determined, i.e. the time at which 50% of the polypeptide circulates in the plasma or is bloodstream prior to being cleared. Determination of serum half-life is often more simple than determining the functional in vivo half-life and the magnitude of serum half-life is usually a good indication of the magnitude of functional in vivo half-life. Alternatively terms to serum half-life include "plasma half-life", "circulating half-life", "serum clearance", "plasma clearance" and "clearance half-life". The polypeptide is cleared by the action of one or more of the reticuloendothelial systems (RES), kidney, spleen or liver, by tissue factor, SEC receptor or other receptor mediated elimination, or by specific or unspecific proteolysis. Normally, clearance depends on size (relative to the cutoff for glomerular filtration), charge, attached carbohydrate chains, and the presence of cellular receptors for the protein. The functionality to be retained is normally selected from procoagulant, proteolytic or receptor binding activity. The functional in vivo half-life and the serum half-life may be determined by any suitable method known in the art.

The term "increased" as used about the functional in vivo half-life or serum half-life is used to indicate that the relevant half-life of the polypeptide variant is statistically significantly increased relative to that of rhFVIIa as determined under comparable conditions (typically determined in an experimental animal, such as rats, rabbits, pigs or monkeys).

The term "$AUC_{iv}$" or "Area Under the Curve when administered intravenously" is used in its normal meaning, i.e. as the area under the activity in serum-time curve, where the polypeptide variant has been administered intravenously, in particular when administered intravenously in rats. Typically, the activity measured is the "clotting activity" as defined hereinbefore. Once the experimental activity-time points have been determined, the $AUC_{iv}$ may conveniently be calculated by a computer program, such as GraphPad Prism 3.01.

It will be understood that in order to make a direct comparison between the $AUC_{iv}$-values of different molecules (e.g. between the variants of the invention and a reference molecule such as rhFVIIa) the same amount of activity should be Administered. Consequently, the $AUC_{iv}$-values are typically normalized (i.e. corrected for differences in the injected dose) and expressed as $AUC_{iv}$/dose Administered.

The term "reduced sensitivity to proteolytic degradation" is primarily intended to mean that the polypeptide variant has reduced sensitivity to proteolytic degradation in comparison to hFVIIa or rhFVIIa as determined under comparable conditions. Preferably, the proteolytic degradation is reduced by at least 10% (e.g. by 10-25% or by 10-50%), such as at least 25% (e.g. by 25-50%, by 25-75% or by 25-100%), more preferably by at least 35%, such as at least 50%, (e.g. by 50-75% or by 50-100%) even more preferably by at least 60%, such as by at least 75% (e.g. by 75-100%) or even at least 90%. Most preferably, the proteolytic degradation is reduced by at least 100%.

The term "renal clearance" is used in its normal meaning to indicate any clearance taking place by the kidneys, e.g. by glomerular filtration, tubular excretion or degradation in the tubular cells. Renal clearance depends on physical characteristics of the polypeptide, including size (diameter), hydrodynamic volume, symmetry, shape/rigidity, and charge. Normally, a molecular weight of about 67 kDa is considered to be a cut-off-value for renal clearance. Renal clearance may be established by any suitable assay, e.g. an established in vivo assay. Typically, renal clearance is determined by administering a labelled (e.g. radiolabelled or fluorescence labelled) polypeptide to a patient and measuring the label activity in urine collected from the patient. Reduced renal clearance is determined relative to a corresponding reference polypeptide, e.g. rhFVIIa, under comparable conditions. Preferably, the renal clearance rate of the polypeptide variant is reduced by at least 50%, preferably by at least 75%, and most preferably by at least 90% compared to rhFVIIa.

The terms "at least 25% of its side chain exposed to the surface of the molecule" and "at least 50% of its side chain exposed to the surface of the molecule" are defined with reference to Example 1, where the calculations, etc. are described in detail.

It should be noted that when the terms "at least 25% of its side chain exposed to the surface of the molecule" and "at least 50% of its side chain exposed to the surface of the molecule" are used in connection with introduction of an in viva N-glycosylation site these terms refer to the surface accessibility of the amino acid side chain in the position where the sugar moiety is actually attached. In many cases it will be necessary to introduce a serine or a threonine residue in position +2 relative to the asparagine residue to which the sugar moiety is actually attached (unless, of course, this position is already occupied by a serine or a threonine residue) and these positions, where the serine or threonine residues are introduced, are allowed to be buried, i.e. to have less than 25% or 50% of their side chains exposed to the surface of the molecule.

The terms "tissue factor binding site", "active site region" and "ridge of the active site binding cleft" are defined with reference to Example 1 herein, wherein the above-mentioned sites/regions are determined.

The term "hydrophobic amino acid residue" includes the following amino acid residues: isoleucine (I), leucine (L), methionine (M), valine (V), phenylalanine (F), tyrosine (Y) and tryptophan (W).

The term "negatively charged amino acid residue" includes the following amino acid residues: Aspartic acid (D) and glutamic acid (E).

The term "positively charged amino acid residue" includes the following amino acid residues: Lysine (K), arginine (R) and histidine (H).

Variants of the Invention

In its broadest aspect the present invention relates to a FVII or FVIIa polypeptide variant having an amino acid sequence comprising 3-15 amino acid modifications relative to hFVII or hFVIIa having the amino acid sequence shown in SEQ ID NO:2, wherein said amino acid sequence of the variant comprises an amino acid substitution in position 10 and 32 and wherein a sugar moiety is covalently attached to an introduced in vivo N-glycosylation site located outside the Gla domain.

The modifications performed in the two above-indicated regions of the parent FVII polypeptide serve the following purposes:

The modifications performed in positions located outside the Gla domain (introduction of in vivo N-glycosylation site(s)) are preferably of such nature that the $AUC_{iv}$, the functional in viva half-life and/or the serum half-life of the resulting variant is increased as compared to rhFVIIa.

The modifications performed in the Gla domain of the parent polypeptide are preferably of such nature that an increased phospholipid membrane binding affinity of the resulting molecule is achieved and/or of such nature the resulting molecule has an improved capability to activate FX to FXa and/or of such nature that a stronger clot is formed.

Without being limited by any particular theory, it is presently believed that the enhanced membrane affinity results in a higher local concentration of the activated polypeptide variants in close proximity to the other coagulation factors, particularly FX. Thus, the rate of activation of FX to FXa will be higher, simply due to a higher molar ratio of the activated FVII variant to FX. The increased activation rate of FX then results in a higher amount of active thrombin, and thus a higher rate of cross-linking of fibrin.

Thus, in preferred embodiments of the invention the parent FVII or FVIIa polypeptide has been modified so that the resulting activated polypeptide variant has (as compared to rhFVIIa):

i) an increased bioavailability ($AUC_{iv}$) and an increased phospholipid membrane binding affinity;
ii) an increased bioavailability ($AUC_{iv}$) and an increased capability to activate FX to FXa;
iii) an increased bioavailability ($AUC_{iv}$) and is capable of generating a stronger clot (increased $AUC_{throm}$);
iv) an increased bioavailability ($AUC_{iv}$) and a reduced $T_{max}$;
v) an increased fractional in vivo half-life and an increased phospholipid membrane binding affinity;
vi) an increased functional in vivo half-life and an increased capability to activate FX to FXa;
vii) an increased functional in vivo half-life and is capable of generating a stronger clot (increased $AUC_{throm}$);
viii) an increased functional in vivo half-life and a reduced $T_{max}$;
ix) an increased serum half-life and an increased phospholipid membrane binding affinity;
x) an increased serum half-life and an increased capability to activate FX to FXa;
xi) an increased serum half-life and is capable of generating a stronger clot (increased $AUC_{throm}$); and/or
xii) an increased serum half-life and a reduced $T_{max}$.

Consequently, medical treatment with a polypeptide variant according to the invention offers a number of advantages over the currently available rhFVIIa compound (NovoSeven®), such as administration of lower dosage, longer duration between injections, increased clot strength and/or faster action.

Thus, preferred variants of the invention are such variants which, in their activated forms and when compared to rhFVIIa, generates in increased Area Under the Curve when administered intravenously ($AUC_{iv}$), in particular when administered intravenously in rats. More particularly, variants of the present invention, which are preferred, are such variants where the ratio between the $AUC_{iv}$ of said variant, in its activated form, and the $AUC_{iv}$ of rhFVIIa is at least 1.25, such as at least 1.5, e.g. at least 1.75, more preferably at least 2, such as at least 3, even more preferably at least 4, such as at least 5, in particular when administered (intravenously) in rats.

This effect may in turn (but do not necessarily do so) correspond to an increased to functional in vivo half-life and/or an increased serum half-life as compared to rhFVIIa. Accordingly, in another preferred embodiment of the invention, the ratio between the functional in vivo half-life or the serum half-life for the variant, in its activated form, and the functional in vivo half-life or the serum half-life for rhFVIIa is at least 1.25. More preferably, the ratio between the relevant half-life for the variant, in its activated form, and the relevant half-life for hFVIIa or rhFVIIa is at least 1.5, such as at least 1.75, e.g. at least 2, even more preferably at least 3, such as at least 4, e.g. at least 5.

As will be understood, the variants of the invention also possess, in addition to the above-mentioned functionality (i.e. increased $AUC_{iv}$, increased functional in viva half-life and/or increased serum half-life), an increased phospholipid membrane binding affinity as compared to rhFVII, an increased capability to activate FX to Fxa, a capability of generating a stronger clot (increased $AUC_{throm}$) and/or a reduced $T_{max}$.

Thus, in one preferred embodiment of the invention, the polypeptide variant has (in addition to an increased $AUC_{iv}$, increased functional in vivo half-life and/or increased serum half-life) an increased phospholipid membrane binding affinity relative to rhFVIIa. Membrane binding affinity may be measured by methods known in the art, such as by the Biacore® assay described in K. Nagata and H. Handa (Ads.), Real-Time Analysis of Biomolecular Interactions, Springer-Verlag, Tokyo, 2000, Chapter 6 entitled "Lipid-Protein Interactions". Alternatively, the membrane binding affinity may be measured as described in Example 1 in WO 99/20767.

In another preferred embodiment of the invention, the polypeptide variant (in addition to an increased $AUC_{iv}$, increased functional in vivo half-life and/or increased serum half-life), has an increased FX activation activity as compared to rhFVIIa, in particular when assayed in a TF-independent assay, such as the "IT-independent Factor X Activation Assay" disclosed herein. More particularly, it is preferred that the ratio between the FX activation activity of the polypeptide variant, in its activated form, and the FX activation activity of rhFVIIa is at least 1.25 when assayed in the "TF-independent Factor X Activation Assay" disclosed herein. More preferably, the ratio between the FX activation activity of the variant, in its activated form, and the FX activation activity of rhFVIIa is at least 1.5, such as at least 1.75, e.g. at least 2, even more preferably at least 3, such as at least 4, e.g. at least 5, still more preferably at least 6, such as at least 7, e.g. at least 8, most preferably at least 9, such as at least 10, when assayed in the "TF-independent Factor X Activation Assay" described herein.

In still another preferred embodiment of the invention, the polypeptide variant is (in addition to an increased $AUC_{iv}$, increased functional in vivo half-life and/or increased serum half-life), in its activated form, capable of generating a stronger clot as compared to rhFVIIa. This effect may be determined in the "Thrombogram Assay" described herein as an increase in the Area Under the Curve ($AUC_{throm}$). The $AUC_{throm}$ is also sometimes denoted "total thrombin work" and constitutes a measure for the strength of the clot formed. More particularly, it is preferred that the ratio between the $AUC_{throm}$, generated by the variant in its activated form, and the $AUC_{throm}$ generated by rhFVIIa is at least 1.15 when assayed in the "Thrombogram Assay" described herein. More preferably, the ratio is at least 1.2, such as at least 1.25, e.g. at least 1.3, even more preferably at least 1.4, such as at least 1.5, e.g. at least 1.6, most preferably at least 1.7, such as at least 1.8, e.g. at least 1.9 or at least 2.

In even another preferred embodiment of the invention the polypeptide variant has (in addition to an increased $AUC_{iv}$, increased functional in vivo half-life and/or increased serum half-life), in its activated form, a faster action. This effect may be determined in the "Thrombogram Assay" described herein as a reduction in the time needed to reach maximum thrombin level ($T_{max}$). Accordingly, preferred variants are such variants where the ratio between $T_{max}$ for the variant, in its activated form, and $T_{max}$ for rhFVIIa is at the most 0.95 when assayed in the "Thrombogram Assay" described herein. Preferably, the ratio is at the most 0.9, such as at the most 0.8, e.g. at the most 0.7, more preferably at the most 0.6, such as at the most 0.5.

Introduction of In Vivo N-glycosylation Sites Located Outside the Gla Domain

A number of suitable modifications leading to an increase in $AUC_{iv}$, functional in vivo half-life and/or serum half-life is disclosed in WO 01/58935. The variants disclosed in WO 01/58935 are the result of a generally new strategy for developing improved FVII or FVIIa molecules, which may also be used for the parent FVII or FVIIa polypeptide of the present invention.

The position to be modified is preferably selected from a part of the FVII or FVIIa molecule that is located outside the tissue factor binding site, and/or outside the active site region, and/or outside the ridge of the active site binding cleft. These sites/regions are identified in Example 1 herein. It should be emphasized, however, that in certain situations, e.g. in case an inactivated polypeptide variant is desired, it may be advantageous to perform modifications in or close to such regions. For example, it is contemplated that one or more in vivo N-glycosylation sites may advantageously be introduced in the active site region or at the ridge of the active site binding cleft of the FVII or FVIIa molecule. The active site region, the tissue factor binding site and the ridge of the active site binding cleft are defined in Example 1 herein and are constituted by the following residues:

I153, Q167, V168, L169, L170, L171, Q176, L177, C178, G179, G180, T181, V188, V189, S190, A191, A192, H193, C194, F195, D196, K197, I198, W201, V228, I229, I230, P231, S232, T233, Y234, V235, P236, G237, T238, T239, N240, H241, D242, I243, A244, L245, L246, V281, S282, G283, W284, G285, Q286, T293, T324, E325, Y326, M327, F328, D338, S339, C340, K341, G342, D343, S344, G345, G346, P347, H348, L358, T359, G360, I361, V362, S363, W364, G365, C368, V376, Y377, T378, R379, V380, Q382, Y383, W386, L387, L400 and F405 (active site region);

L13, K18, F31, E35, R36, L39, F40, I42, S43, S60, I062, D63, Q64, L65, I69, C70, F71, C72, L73, P74, F76, E77, G78, R79, S82, K85, Q88, I90, V92, N93, E94, S271, A274, F275, V276, R277, F278, S304, L305, M306, T307, Q308, D309, Q312, Q313, S325 and R379 (tissue factor binding site); and N173, A175, K199, N200, N203, D289, R290, G291, A292, P321 and T370 (the ridge of the active site binding cleft).

The total number of amino acid residues to be modified outside the Gla domain in the parent FVII or FVIIa polypeptide (as compared to the amino acid sequence shown in SEQ ID NO:2) will typically not exceed 10. Preferably, the FVII or FVIIa variant comprises an amino acid sequence which differs in 1-10 amino acid residues from amino acid residues 46-406 shown in SEQ ID NO:2, typically in 1-8 or in 2-8 amino acid residues, e.g. in 1-5 or in 2-5 amino acid residues, such as in 1-4 or in 1-3 amino acid residues, e.g. in 1, 2 or 3 amino acid residues from amino acid residues 46-406 shown in SEQ ID NO:2.

Thus, the polypeptide variant of the invention may contain 1-10 (additional or introduced) in vivo N-glycosylation sites, typically 1-8 or 2-8 (additional or introduced) in vivo N-glycosylation sites, preferably 1-5 or 2-5 (additional or introduced) in viva N-glycosylation sites, such as 1-4 or 1-3 (additional or introduced) in vivo N-glycosylation sites, e.g. 1, 2 or 3 (additional or introduced) in vivo N-glycosylation sites. Analogously, the polypeptide variant of the invention may contain 1-10 (additional or introduced) sugar moieties, typically 1-8 or 2-8 (additional or introduced) sugar moieties, preferably 1-5 or 2-5 (additional or introduced) sugar moieties, such as 1-4 or 1-3 (additional or introduced) sugar moieties, e.g. 1, 2 or 3 (additional or introduced) sugar moieties. It will be understood that the introduced sugar moiety/moieties will be covalently attached to the introduced in vivo N-glycosylation site(s)

When used in the present context, the term "naturally occurring glycosylation site" covers the glycosylation sites at positions N145, N322, S52 and S60. In a similar way, the term "naturally occurring in vivo O-glycosylation site" includes the positions 552 and S60, whereas the term "naturally occurring in vivo N-glycosylation site" includes positions N145 and N322.

It will be understood that in order to prepare a polypeptide variant, wherein the polypeptide variant comprises one or more sugar moieties covalently attached to one or more in vivo N-glycosylation sites, the polypeptide variant must be expressed in a host cell capable of attaching sugar (oligosaccharide) moieties at the glycosylation site(s) or alternatively subjected to in vitro glycosylation. Examples of glycosylating host cells are given in the section further below entitled "Coupling to a sugar moiety".

Examples of positions, wherein the in vivo N-glycosylation sites may be introduced include, but is not limited to, positions comprising an amino acid residue having an amino acid residue having at least 25% of its side chain exposed to the surface (as defined in Example 1 herein), such as in a position comprising an amino acid residue having at least 50% of its side chain exposed to the surface (as defined in Example 1 herein). In general, it is preferred that the in vivo N-glycosylation site is introduced by substitution, although insertion is also contemplated. The position is preferably selected from a part of the molecule that is located outside the tissue factor binding site and/or the active site region and/or outside the ridge of the active site cleft. These sites/regions are identified in Example 1 herein. It should be understood that when the term "at least 25% (or at least 50%) of its side chain exposed to the surface" is used in connection with introduction of an in vivo N-glycosylation site this term refers to the surface accessibility of the amino acid side chain in the position where the sugar moiety is actually attached. In many cases it will be necessary to introduce a serine or a threonine residue in position +2 relative to the asparagine residue to which the sugar moiety is actually attached (unless, of course, this position is already occupied by a serine or a threonine residue) and these positions, where the serine or threonine residues are introduced, are allowed to be buried, i.e. to have less than 25% of their side chains exposed to the surface.

Specific and preferred examples of such substitutions creating an in vivo N-glycosylation site include a substitution selected from the group consisting of A51N, 058N, T106N, K109N, G124N, K143N+N145T, A175T, I2055, I205T, V253N, T267N, T267N+S269T, S314N+K316S, S314N+K3161, R315N+V317S, R315N+V317T, K316N+G318S, K316N+G318T, G318N, D334N and combinations thereof. More preferably, the in vivo N-glycosylation site is introduced by a substitution selected from the group consisting of A51N, G58N, T106N, K109N, G124N, K143N+N145T, A175T, I205T, V253N, T267N+S269T, S314N+K316T, R315N+V317T, K316N+G318T, G318N, D334N and combinations thereof. Even more preferably, the in vivo N-glycosylation site is introduced by a substitution selected from the group consisting of T106N, A175T, I205T, V253N, T267N+S269T and combinations thereof, in particular I205T.

In one embodiment, only one in vivo N-glycosylation site has been introduced by substitution. In another embodiment, two or more (such as two) in vivo N-glycosylation sites have been introduced by substitution. Examples of preferred substitutions creating two in vivo N-glycosylation sites include substitutions selected from the group consisting of A51N+G58N, A51N+T106N, A51N+K109N, A51N+G124N, A51N+K143N+N145T, A51N+A175T, A51N+I205T, A51N+V253N, A51N+T267N+S269T, A51N+S314N+K316T, A51N+R315N+V317T, A51N+K316N+G318T, A51N+G318N, A51N+D334N, G58N+T106N, G58N+K109N, G58N+G124N, G58N+K143N+N145T, G58N+A175T, G58N+I205T, G58N+V253N, G58N+T267N+S269T, G58N+S314N+K316T, G58N+R315N+V317T, G58N+K316N+G318T, G58N+G318N, G58N+D334N, T106N+K109N, T106N+G124N, T106N+K143N+N145T, T106N+A175T, T106N+I205T, T106N+V253N, T106N+T267N+S269T, T106N+S314N+K316T, T106N+R315N+V317T, T106N+K316N+G318T, T106N+G318N, T106N+D334N, K109N+G124N, K109N+K143N+N145T, K109N+A175T, K109N+I205T, K109N+V253N, K109N+T267N+S269T, K109N+S314N+K316T, K109N+R315N+V317T, K109N+K316N+G318T, K109N+G318N, K109N+D334N, G124N+K143N+N145T, G124N+A175T, G124N+I205T, 0124N+V253N, G124N+T267N+S269T, G124N+S314N+K316T, G124N+R315N+V317T, G124N+K316N+G318T, G124N+G318N, G124N+D334N, K143N+N145T+A175T, K143N+N145T+I205T, K143N+N145T+V253N, K143N+N145T+T267N+S269T, K143N+N145T+S314N+K316T, K143N+N145T+R315N+V317T, K143N+N145T4-K316N+G318T, K143N+N145T+G318N, K143N+N145T+D334N, A175T+I205T, A175T+V253N, A175T+T267N+S269T, A175T+S314N+K316T, A175T+R315N+V317T, A175T+K316N+G318T, A175T+G318N, A175T+D334N, I205T+V253N, I205T+T267N+S269T, I205T+S314N+K316T, I205T+R315N+V317I, I205T+K316N+G318T, I205T+G318N, I205T+D33414, V253N+T267N+S269T, V253N+S314N+K316T, V253N+R315N+V317T, V253N+K316N+G318T, V253N+G318N, V253N+D334N, T267N+S269T+S314N+K316T, T267N+S269T+R315N+V317T, T267N+S269T+K316N+G318T, 1267N+S269T+G318N, T267N+S269T+D334N, S314N+K316T+R315N+V317T, S314N+K316T+G318N, S314N+K316T+D334N, R315N+V317T+K316N+G318T, R315N+V317T+G318N, R315N+V317T+D334N and G318N+D334N. More preferably, the substitutions are selected from the group consisting of T106N+A175T, T106N+I205T, T106N+V253N, T106N+T267N+S269T, A175T+I205T, A175T+V253N, A175T+T267N+S269T, I205T+V253N, I205T+1267N+S269T and V253N+T267N+S269T, even more preferably from the group consisting of T106N+I205T, T106N+V253N and I205T+T267N+S269T.

In an even further embodiment, three or more (such as three) in vivo N-glycosylation sites have been introduced by substitution. Examples of preferred substitutions creating three in vivo N-glycosylation sites include substitutions selected from the group consisting of I205T+V253N+T267N+S269T and T106N+I205T+V253N.

As discussed above, it is preferred that the in vivo N-glycosylation site is introduced in a position which does neither form part of the tissue factor binding site nor form part of the active site region and the ridge of the active site binding cleft as defined herein. It is envisaged that such glycosylation variants will primarily belong to the class of active polypeptide variants as defined hereinbefore.

It will be understood that as an alternative to introduction of in vivo N-glycosylation sites in the above-discussed positions one may introduce (either by substitution or by insertion) cysteine residues in the same positions, where the introduced cysteine residue is then subsequently covalently attached to a non-polypeptide moiety, such as PEG, in particular mPEG. Thus, examples of positions, wherein a cysteine residue may be introduced include, but is not limited to, positions comprising an amino acid residue having an amino acid residue having at least 25% of its side chain exposed to the surface (as defined in Example 1 herein), such as in a position comprising an amino acid residue having at least 50% of its side chain exposed to the surface (as defined in Example 1 herein). The position is preferably selected from a part of the molecule that is located outside the tissue factor binding site and/or the active site region and/or outside the ridge of the active site cleft. These sites/regions are identified in Example 1 herein. Thus, the above disclosure concerning introduction of in vivo N-glycosylation sites applies mutatis mutandis to introduction of cysteine residues.

It will be understood that the modifications in positions located outside the Gla domain discussed in the above section should be combined with one or more modifications in the Gla domain (see the section entitled "Modifications in the Gla domain" below).

Modifications in the Gla Domain

As will be understood the variants of the present invention comprises, in addition to at least one introduced in vivo N-glycosylation site located outside the Gla domain (cf. above), at least two substitutions in the Gla domain, namely a substitution in position 10 and position 32.

A number of suitable modifications leading to increased phospholipid membrane to binding affinity is disclosed in WO 99/20767 and WO 00/66753.

In a preferred embodiment of the invention the substitution in position 10 is P10Q. In another preferred embodiment of the invention the substitution in position 32 is K32E. In a particularly preferred embodiment of the invention the variant comprises the following substitutions P10Q+K32E.

In an interesting embodiment of the invention the variant comprises, in addition to the substitutions in position 10 and 32, such as in addition to the substitutions P10Q+102E, at least one further modification in the Gla domain.

In one preferred embodiment of the invention the further modification in the Gla domain comprises an amino acid substitution in position 33. Preferably, a hydrophobic amino acid residue is introduced by substitution in position 33, such as D33I, D33L, D33M, D33V, D33F, D33Y or D33W, in particular D33F. Accordingly, in one very interesting embodiment of the invention, the variant comprises the following substitutions P10Q+K32+D33F.

In another preferred embodiment of the invention the further modification in the Gla domain comprises an insertion of at least one (such as one) amino acid residue between position 3 and 4. It is preferred that the inserted amino acid residue is a hydrophobic amino acid residue. Most preferably the insertion is A3AY. Accordingly, in another very interesting embodiment of the invention, the variant comprises the following modifications A3AY+P10Q+K32E or A3AY+P10Q+K32E+D33F.

In still another preferred embodiment of the invention the further modification in the Gla domain comprises a substitution in position 34. It is preferred that a negatively charged amino acid residue is introduced by substitution in position 34. Most preferably the substitution is A34E. Accordingly, in still another very interesting embodiment of the invention, the variant comprises the following modifications P10Q+K32E+A34E, P10Q+K32E+D33F+A34E, A3AY+P 10Q+K32E+A34E or A3AY+P10Q+K32E+D33F+A34E.

The Gla domain may also contain modifications in other positions, in particular in positions 8, 11 and 28, such as R28F or R28E. On the other hand it should be understood that the Gla domain should not be modified to such an extent that the membrane binding properties are impaired. Accordingly, it is preferred that no modifications are made in the residues that become γ-carboxylated, i.e. it is preferred that no modifications are made in residues 6, 7, 14, 16, 19, 20, 25, 26, 29 and 35. In a similar way, it is in general not preferred that non-polypeptide moieties, such as sugar moieties and/or PEG groups, are introduced in the Gla domain. Consequently, it is preferred that no modifications are made in the Gla domain that creates an in vivo N-glycosylation site.

Finally, it will be understood that the modifications in the Gla domain discussed in this section must be combined with one or more of the modifications disclosed in the section entitled "Introduction of in vivo N-glycosylation sites located outside the Gla domain" above.

Specific examples of such "combined" variants are given below.

In one embodiment of the invention said FVII or FVIIa variant comprises the following modifications: P10Q+K32E+T106N.

In a further embodiment of the invention said FVII or FVIIa variant comprises the following modifications: P10Q+K32E+A175T.

In a further embodiment of the invention said FVII or FVIIa variant comprises the following modifications: P10Q-1-K32E44205T.

In a further embodiment of the invention said FVII or FVIIa variant comprises the following modifications: P10Q+K32E+V253N.

In a further embodiment of the invention said FVII or FVIIa variant comprises the following modifications: P10Q+K32E+T267+S269T.

In a further embodiment of the invention said FVII or FVIIa variant comprises the following modifications: P10Q+K32E+T106N+I205T.

In a further embodiment of the invention said FVII or FVIIa variant comprises the following modifications: P10Q+K32E+T106N+V253N.

In a further embodiment of the invention said FVII or FVIIa variant comprises the following modifications: P10Q+K32E+I205T+T267N+S269T.

In a further embodiment of the invention said FVII or FVIIa variant comprises the following modifications: A3AY+P10Q+K32E+T106N.

In a further embodiment of the invention said FVII or FVIIa variant comprises the following modifications: A3AY+P10Q+K32E+A 175T.

In a further embodiment of the invention said FVII or FVIIa variant comprises the following modifications: A3AY+P10Q+K32E+I205T.

In a further embodiment of the invention said FVII or FVIIa variant comprises the following modifications: A3AY+P10Q+K32E+V253N.

In a further preferred embodiment of the invention said FVII or FVIIa variant comprises the following modifications: A3AY+P10Q+K32E+T267+S269T.

In a further embodiment of the invention said FVII or FVIIa variant comprises the following modifications: A3AY+P10Q+K32E+T106N+I205T.

In a further embodiment of the invention said FVII or FVIIa variant comprises the to following modifications: A3AY+P10Q+K32E+T106N+V253N.

In a further embodiment of the invention said FVII or FVIIa variant comprises the following modifications: A3AY+P10Q+K32E+I205T+T267N+S269T.

In a further embodiment of the invention said FVII or FVIIa variant comprises the following modifications: P10Q+K32E+D33F+T106N.

In a further embodiment of the invention said FVII or FVIIa variant comprises the following modifications: P10Q+K32E+D33F+A175T.

In a further embodiment of the invention said FVII or FVIIa variant comprises the following modifications: P10Q+K32E+D33F+I205T.

In a further embodiment of the invention said FVII or FVIIa variant comprises the following modifications: P10Q+K32E+D33F+V253N.

In a further embodiment of the invention said FVII or FVIIa variant comprises the following modifications: P10Q+K32E+D33F+T267+S269T.

In a further embodiment of the invention said FVII or FVIIa variant comprises the following modifications: P10Q+K32E+D33F+T106N+I205T. In a further embodiment of the invention said FVII or FVIIa variant comprises the following modifications: P10Q+K32E+D33F+T106N+V253N.

In a further embodiment of the invention said FVII or FVIIa variant comprises the following modifications: P10Q+K32E+D33F+I205T+T267N+S269T.

In a further embodiment of the invention said FVII or FVIIa variant comprises the following modifications: A3AY+P10Q+K32E+D33F+T106N.

In a further embodiment of the invention said FVII or FVIIa variant comprises the following modifications: A3AY+P10Q+K32E+D33F+A175T.

In a further embodiment of the invention said FVII or FVIIa variant comprises the following modifications: A3AY+P10Q+K32E+D33F+I205T.

In a further embodiment of the invention said FVII or FVIIa variant comprises the following modifications: A3AY+P10Q+K32E+D33F+V253N.

In a further embodiment of the invention said FVII or FVIIa variant comprises the following modifications: A3AY+P10Q+K32E+D33F+T267+S269T.

In a further embodiment of the invention said FVII or FVIIa variant comprises the following modifications: A3AY+P10Q+102E+D33F+T106N+I205T.

In a further embodiment of the invention said FVII or FVIIa variant comprises the following modifications: A3AY+P10Q+K32E+D33F+T106N+V253N.

In a further embodiment of the invention said FVII or FVIIa variant comprises the to following modifications: A3AY+P10Q+K32E+D33F+I205T+T267N+S269T.

In a further embodiment of the invention said FVII or FVIIa variant comprises the following modifications: P10Q+132E+A34E+T106N.

In a further embodiment of the invention said FVII or FVIIa variant comprises the following modifications: P10Q+K32E+A34E+A175T.

In a further embodiment of the invention said FVII or FVIIa variant comprises the following modifications: P10Q+K32E+A34E+I205T.

In a further embodiment of the invention said FVII or FVIIa variant comprises the following modifications: P10Q+K32E+A34E+V253N.

In a further embodiment of the invention said FVII or FVIIa variant comprises the following modifications: P10Q+K32E+A34E+T267+S269T.

In a further embodiment of the invention said FVII or FVIIa variant comprises the following modifications: P10Q+K32E+A34E+T106N+I205T.

In a further embodiment of the invention said FVII or FVIIa variant comprises the following modifications: P10Q+K32E+A34E+T106N+V253N.

In a further embodiment of the invention said FVII or FVIIa variant comprises the following modifications: P10Q+K32E+A34E+I205T+T267N+S269T.

In a further embodiment of the invention said FVII or FVIIa variant comprises the following modifications: P10Q+I02E+D33F+A34E+T106N.

In a further embodiment of the invention said FVII or FVIIa variant comprises the following modifications: P10Q+I02E+D33F+A34E A175T.

In a further embodiment of the invention said FVII or FVIIa variant comprises the following modifications: P10Q+K32E+D33F+A34E+I205T.

In a further embodiment of the invention said FVII or FVIIa variant comprises the following modifications: P10Q+K32E+D33F+A34E V253N.

In a further embodiment of the invention said FVII or FVIIa variant comprises the following modifications: P10Q+I32E+D33F+A34E+T267+S269T.

In a further embodiment of the invention said FVII or FVIIa variant comprises the following modifications: P10Q+K32E+D33F+A34E T106N+I205T.

In a further embodiment of the invention said FVII or FVIIa variant comprises the following modifications: P10Q+I02E+D33F+A34E T106N+V253N.

In a further embodiment of the invention said FVII or FVIIa variant comprises the following modifications: P10Q+I02E+D33F+A34E+I205T+T267N+S269T.

In a further embodiment of the invention said FVII or FVIIa variant comprises the following modifications: A3AY+P10Q+K32E+A34E+T106N.

In a further embodiment of the invention said FVII or FVIIa variant comprises the following modifications: A3AY+P10Q+K32E+A34E A175T.

In a further embodiment of the invention said FVII or FVIIa variant comprises the following modifications: A3AY+P10Q1-K32E+A34E+I205T. In a further embodiment of the invention said FVII or FVIIa variant comprises the following modifications: A3AY+P10Q+K32E+A34E V253N.

In a further embodiment of the invention said FVII (or FVIIa variant comprises the following modifications: A3AY+P10Q+K32E+A34E T267+S269T.

In a further embodiment of the invention said FVII or FVIIa variant comprises the following modifications: A3AY+P10Q+K32E+A34E T106N+I205T.

In a further embodiment of the invention said FVII or FVIIa variant comprises the following modifications: A3AY+P10Q+K32E+A34E T106N+V253N.

In a further embodiment of the invention said FVII or FVIIa variant comprises the following modifications: A3AY+P10Q+K32E+A34E+I205T+T267N+8269T.

In a further embodiment of the invention said FVII or FVIIa variant comprises the following modifications: A3AY+P10Q+K32E+D33F+A34E+T106N.

In a further embodiment of the invention said FVII or FVIIa variant comprises the following modifications: A3AY+P10Q+K32E+D33F+A34E A175T.

In a further embodiment of the invention said FVII or FVIIa variant comprises the following modifications: A3AY+P10Q+K32E+D33F+A34E+I205T.

In a further embodiment of the invention said FVII or FVIIa variant comprises the following modifications: A3AY+P10Q+K32E+D33F+A34E V253N.

In a further embodiment of the invention said FVII or FVIIa variant comprises the following modifications: A3AY+P10Q+K32E+D33F+A34E T267+S269T.

In a further embodiment of the invention said FVII or FVIIa variant comprises the following modifications: A3AY+P10Q+K32E+D33F+A34E T106N+I205T.

In a further embodiment of the invention said FVII or FVIIa variant comprises the following modifications: A3AY+P10Q+K32E+D33F+A34E T106N+V253N.

In a further embodiment of the invention said FVII or FVIIa variant comprises the following modifications: A3AY+P10Q+K32E+D33F+A34E+I205T+T267N+S269T.

Other Modifications Outside the Gla Domain

In a further embodiment of the present invention, the FVII or FVIIa variant may, in addition to the modifications described in the sections above, also contain mutations, which are already known to increase the intrinsic activity of the polypeptide, e.g. such as those described in WO 02/22776

Examples of preferred substitutions include substitutions selected from the group consisting of V158D, E296D, M298Q, L305V and K337A. More preferably, said substitutions are selected from the group consisting of V158D+E296D+M298Q+L305V+K337A, V158D+E296D+M298Q+K337A, V158D+E296D+M298Q+L305V, V158D+E296D+M298Q, M298Q, L305V+K337A, L305V and K337A.

In a further embodiment of the present invention, the FVII or FVIIa variant may, in addition to the modifications described in the sections above, also contain mutations, which are already known to cause a decreased inhibition by TFPI. One example includes the substitution K341Q disclosed by Neuenschwander et al, Biochemistry, 1995; 34:8701-8707.

Moreover, the variant may contain modifications which are believed to increase the TF binding affinity. Examples of such modifications include substitutions selected from the group consisting of L39E, L39Q, L39H, 142K, 142R, S43H, S43Q, K62E, K62R, L65Q, L65S, F71D, F71Y, F71E, F71Q, F71N, E82Q, E82N, E82K and F275H As already indicated above, the variant may also contain conservative amino acid substitutions.

The Non-polypeptide Moiety

Based on the present disclosure the killed person will be aware that amino acid residues comprising other attachment groups may be introduced by substitution into the parent polypeptide, using the same approach as that illustrated above with in vivo N-glycosylation sites. For instance, one or more amino acid residues comprising an acid group (glutamic acid or aspartic acid), tyrosine or lysine may be introduced into the positions discussed above. In particular, one or more cysteine residues may be introduced in the positions discussed above.

As indicated further above the non-polypeptide moiety of the conjugated variant is preferably selected from the group consisting of a polymer molecule, a lipophilic compound, a sugar moiety (by way of in vivo glycosylation) and an organic derivatizing agent. All of these agents may confer desirable properties to the variant polypeptide, in particular increased $AUC_{iv}$, increased functional in vivo half-life and/or increased plasma half-life. The variant polypeptide is normally conjugated to only one type of non-polypeptide moiety, but may also be conjugated to two or more different types of non-polypeptide moieties, e.g. to a polymer molecule and a sugar moiety, to a lipophilic group and a sugar moiety, to an organic derivatizing agent and a sugar moiety, to a lipophilic group and a polymer molecule, etc. The conjugation to two or more different non-polypeptide moieties may be done simultaneous or sequentially.

Methods of Preparing a Conjugated Variant of the Invention

In the following sections "Conjugation to a lipophilic compound", "Conjugation to a polymer molecule", "Conjugation to a sugar moiety" and "Conjugation to an organic derivatizing agent" conjugation to specific types of non-polypeptide moieties is described. In general, a conjugated variant according to the invention may be produced by culturing an appropriate host cell under conditions conducive for the expression of the variant polypeptide, and recovering the variant polypeptide, wherein a) the variant polypeptide comprises at least one N- or O-glycosylation site and the host cell is an eukaryotic host cell capable of in vivo glycosylation, and/or b) the variant polypeptide is subjected to conjugation to a non-polypeptide moiety in vitro.

It will be understood that the conjugation should be designed so as to produce the optimal molecule with respect to the number of non-polypeptide moieties attached, the size and form of such molecules (e.g. whether they are linear or branched), and the attachment site(s) in the polypeptide. The molecular weight of the non-polypeptide moiety to be used may, e.g., be chosen on the basis of the desired effect to be achieved. For instance, if the primary purpose of the conjugation is to achieve a conjugated variant having a high molecular weight (e.g. to so reduce renal clearance) it is usually desirable to conjugate as few high molecular weight non-polypeptide moieties as possible to obtain the desired molecular weight. When a high degree of shielding is desirable this may be obtained by use of a sufficiently high number of low molecular weight non-polypeptide moieties (e.g. with a molecular weight of from about 300 Da to about 5 kDa, such as a molecular weight of from 300 Da to 2 kDa).

Conjugation to a Polymer Molecule

The polymer molecule to be coupled to the variant polypeptide may be any suitable polymer molecule, such as a natural or synthetic homo-polymer or hetero-polymer, typically with a molecular weight in the range of about 300-100,000 Da, such as about 500-20,000 Da, more preferably in the range of about 500-15,000 Da, even more preferably in the range of about 2-12 kDa, such as in the range of about 3-10 kDa. When the term "about" is used herein in connection with a certain molecular weight, the word "about" indicates an approximate average molecular weight and reflects the fact that there will normally be a certain molecular weight distribution in a given polymer preparation.

Examples of homo-polymers include a polyol (i.e. poly-OH), a polyamine (i.e. poly-$NH_2$) and a polycarboxylic acid (i.e. poly-COOH). A hetero-polymer is a polymer comprising different coupling groups, such as a hydroxyl group and an amine group.

Examples of suitable polymer molecules include polymer molecules selected from the group consisting of polyalkylene oxide (PAO), including polyalkylene glycol (PAG), such as polyethylene glycol (PEG) and polypropylene glycol (PPG), branched PEGs, poly-vinyl alcohol (PVA), poly-carboxylate, poly-(vinylpyrolidone), polyethylene-co-maleic acid anhydride, polystyrene-co-maleic acid anhydride, dextran, including carboxymethyl-dextran, or any other biopolymer suitable for reducing immunogenicity and/or increasing functional in vivo half-life and/or serum half-life. Another example of a polymer molecule is human albumin or another abundant plasma protein. Generally, polyalkylene glycol-derived polymers are biocompatible, non-toxic, non-antigenic, non-immunogenic, have various water solubility properties, and are easily excreted from living organisms.

PEG is the preferred polymer molecule, since it has only few reactive groups capable of cross-linking compared to, e.g., polysaccharides such as dextran. In particular, mono-functional PEG, e.g. methoxypolyethylene glycol (mPEG), is of interest since its coupling chemistry is relatively simple (only one reactive group is available for conjugating with attachment groups on the polypeptide). Consequently, as the risk of cross-linking is eliminated, the resulting conjugated variants are more homogeneous and the reaction of the polymer molecules with the variant polypeptide is easier to control.

To effect covalent attachment of the polymer molecule(s) to the variant polypeptide, the hydroxyl end groups of the polymer molecule must be provided in activated form, i.e. with reactive functional groups (examples of which include primary amino groups, hydrazide (HZ), thiol, succinate (SUC), succinimidyl succinate (SS), succinimidyl suctinamide (SSA), succinimidyl propionate (SPA), succinimidyl butyrate (SBA), succinimidy carboxymethylate (SCM), benzotriazole carbonate (BTC), N-hydroxysuccinimide (NHS), aldehyde, nitrophenylcarbonate (NPC), and tresylate (TRES)). Suitable activated polymer molecules are commercially available, e.g. from Shearwater Polymers, Inc., Huntsville, Ala., USA, or from PolyMASC Pharmaceuticals plc, UK.

Alternatively, the polymer molecules can be activated by conventional methods known in the art, e.g. as disclosed in WO 90/13540. Specific examples of activated linear or branched polymer molecules for use in the present invention are described in the Shearwater Polymers, Inc. 1997 and 2000 Catalogs (Punctionalized Biocompatible Polymers for Research and pharmaceuticals, Polyethylene Glycol and Derivatives, incorporated herein by reference).

Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG, BTC-PEG, EPDX-PEG, NCO-PEG, NPC-PEG, CDI-PEG, ALD-PEG, TRES-PEG, VS-PEG, IODO-PEG, and MAL-PEG, and branched PEGS such as PEG2-NHS and those disclosed in U.S. Pat. Nos. 5,932,462 and 5,643,575, both of which are incorporated herein by reference. Furthermore, the following publications, incorporated herein by reference, disclose useful polymer molecules and/or PEGylation chemistries: U.S. Pat. Nos. 5,824,778, 5,476,653, WO 97/32607, EP 229,108, EP 402, 378, U.S. Pat. Nos. 4,902,502, 5,281,698, 5,122,614, 5,219, 564, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629,384, WO 96/41813, WO 96/07670, U.S. Pat. Nos. 5,473,034, 5,516, 673, EP 605 963, U.S. Pat. No. 5,382,657, EP 510 356, EP 400 472, EP 183 503 and EP 154 316.

Specific examples of activated PEG polymers particularly preferred for coupling to cysteine residues, include the following linear PEGs: vinylsulfone-PEG (VS-PEG), preferably vinylsulfone-mPEG (VS-mPEG); maleimide-PEG (MAL-PEG), preferably maleizaide-mPEG (MAL-mPEG) and orthopyridyl-disulfide-PEG (OPSS-PEG), preferably orthopyridyl-distade-mPEG (OPSS-mPEG). Typically, such PEG or mPEG polymers will have a size of about 5 kDa, about 10 kD, about 12 kDa or about 20 kDa.

The conjugation of the polypeptide variant and the activated polymer molecules is conducted by use of any conventional method, e.g. as described in the following references (which also describe suitable methods for activation of polymer molecules): Harris and Zalipsky, eds., Poly(ethylene glycol) Chemistry and Biological Applications, AZC, Washington; R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.).

The skilled person will be aware that the activation method and/or conjugation chemistry to be used depends on the attachment group(s) of the variant polypeptide (examples of which are given further above), as well as the functional groups of the polymer (e.g. being amine, hydroxyl, carboxyl, aldehyde, sulfydryl, succinimidyl, maleimide, vinysulfone or to haloacetate). The PEGylation may be directed towards conjugation to all available attachment groups on the variant polypeptide (i.e. such attachment groups that are exposed at the surface of the polypeptide) or may be directed towards one or more specific attachment groups, e.g. the N-terminal amino group as described in U.S. Pat. No. 5,985,265 or to cysteine residues. Furthermore, the conjugation may be achieved in one step or in a stepwise manner (e.g. as described in WO 99/55377).

For PEGylation to cysteine residues (see above) the FVII or FVIIa variant is usually treated with a reducing agent, such as dithiothreitol (DDT) prior to PEGylation. The reducing agent is subsequently removed by any conventional method, such as by desalting. Conjugation of PEG to a cysteine residue typically takes place in a suitable buffer at pH 6-9 at temperatures varying from 4° C. to 25° C. for periods up to 16 hours.

It will be understood that the PEGylation is designed so as to produce the optimal molecule with respect to the number of PEG molecules attached, the size and form of such molecules (e.g. whether they are linear or branched), and the attachment site(s) in the variant polypeptide. The molecular weight of the polymer to be used may e.g. be chosen on the basis of the desired effect to be achieved.

In connection with conjugation to only a single attachment group on the protein (e.g. the N-terminal amino group), it may be advantageous that the polymer molecule, which may be linear or branched, has a high molecular weight, preferably about 10-25 kDa, such as about 15-25 kDa, e.g. about 20 kDa.

Normally, the polymer conjugation is performed under conditions aimed at reacting as many of the available polymer attachment groups with polymer molecules. This is achieved by means of a suitable molar excess of the polymer relative to the polypeptide. Typically, the molar ratios of activated polymer molecules to polypeptide are up to about 1000-1, such as up to about 200-1, or up to about 100-1. In some cases the ration may be somewhat lower, however, such as up to about 50-1, 10-1, 5-1, 2-1 or 1-1 in order to obtain optimal reaction.

It is also contemplated according to the invention to couple the polymer molecules to the polypeptide through a linker. Suitable linkers are well known to the skilled person. A preferred example is cyanuric chloride (Abuchowski et al., (1977), J. Biol. Chem., 252, 3578-3581; U.S. Pat. No. 4,179, 337; Shafer et al., (1986), J. Polym. Sci. Polym. Chem. Ed., 24, 375-378).

Subsequent to the conjugation, residual activated polymer molecules are blocked according to methods known in the art, e.g. by addition of primary amine to the reaction mixture, and the resulting inactivated polymer molecules are removed by a suitable method.

It will be understood that depending on the circumstances, e.g. the amino acid sequence of the variant polypeptide, the nature of the activated PEG compound being used and the specific PEGylation conditions, including the molar ratio of PEG to polypeptide, varying degrees of PEGylation may be obtained, with a higher degree of PEGylation generally being obtained with a higher ratio of PEG to variant polypeptide. The PEGylated variant polypeptides resulting from any given PEGylation process will, however, normally comprise a stochastic distribution of conjugated polypeptide variants having slightly different degrees of PEGylation.

Coupling to a Sugar Moiety

In order to achieve in vivo glycosylation of a FVII molecule comprising one or more glycosylation sites the nucleotide sequence encoding the variant polypeptide must be inserted in a glycosylating, eucaryotic expression host. The expression host cell may be selected from fungal (filamentous fungal or yeast), insect or animal cells or from transgenic plant cells. In one embodiment the host cell is a mammalian cell, such as a CHO cell, BIM or HEK, e.g. HEK 293, cell, or an insect cell, such as an SF9 cell, or a yeast cell, e.g. *S. cerevisiae* or *Pichia pastoris*, or any of the host cells mentioned hereinafter.

Covalent in vitro coupling of sugar moieties (such as dextran) to amino acid residues of the variant polypeptide may also be used, e.g. as described, for example in WO 87/05330 and in Aplin et al., CRC Crit. Rev. Biochem, pp. 259-306, 1981. The in vitro coupling of sugar moieties or PEG to protein- and peptide-bound Gln-residues can be carried out by transglutaminases (TGases). Transglutaminases catalyse the transfer of donor amine-groups to protein- and peptide-bound Gln-residues in a so-called cross-linking reaction. The donor-amine groups can be protein- or peptide-bound, such as the s-amino-group in Lys-residues or it can be part of a small or large organic molecule. An example of a small organic molecule functioning as amino-donor in TGase-catalysed cross-linking is putrescine (1,4-diaminobutane). An example of a larger organic molecule functioning as amino-donor in TGase-catalysed cross-linking is an amine-containing PEG (Sato et al., 1996, Biochemistry 35, 13072-13080).

TGases, in general, are highly specific enzymes, and not every Gln-residues exposed on the surface of a protein is accessible to TGase-catalysed cross-linking to amino-containing substances. On the contrary, only few Gln-residues are naturally functioning as TGase substrates but the exact parameters governing which Gln-residues are good TGase substrates remain unknown. Thus, in order to render a protein susceptible to TGase-catalysed cross-linking reactions it is often a prerequisite at convenient positions to add stretches of amino acid sequence known to function very well as TGase substrates. Several amino acid sequences are known to be or to contain excellent natural TGase substrates e.g. substance P, elafin, fibrinogen, fibronectin, $\alpha_2$-plasmin inhibitor, $\alpha$-caseins, and $\beta$-caseins.

Conjugation to an Organic Derivatizing Agent

Covalent modification of the variant polypeptide may be performed by reacting one or more attachment groups of the variant polypeptide with an organic derivatizing agent. Suitable derivatizing agents and methods are well known in the art. For example, cysteinyl residues most commonly are reacted with $\alpha$-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, $\alpha$-bromo-$\beta$-(4-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues are derivatized by reaction with diethylpyrocarbonate at pH 5.5-7.0 because this agent is relatively specific for the histidyl side chain. Para-bromophenacyl bromide also is useful. The reaction is preferably performed in 0.1 M sodium cacodylate at pH 6.0. Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione and transaminase-catalyzed reaction with glyoxylate. Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group.

Furthermore, these reagents may react with the groups of lysine as well as the arginine guanidino group. Carboxyl side groups (aspartyl or glutamyl) are selectively modified by reaction with carbodiimides (R—N=C=N—R'), where R and R' are different alkyl groups, such as 1-cyclohexyl-3(2-morpholinyl-4-ethyl) carbodiimide or 1-ethyl-3-(4-azonia-4,4 dimethylpentyl)carbodiimide. Furthermore, aspartyl and glutamyl residues are converted to asparaginyl and glutaminyl residues by reaction with ammonium ions.

Conjugation to a Lipophilic Compound

The variant polypeptide and the lipophilic compound may be conjugated to each other, either directly or by use of a linker. The lipophilic compound may be a natural compound such as a saturated or unsaturated fatty acid, a fatty acid diketone, a terpene, a prostaglandin, a vitamin, a carotenoide or steroide, or a synthetic compound such as a carbon acid, an alcohol, an amine and sulphonic acid with one or more alkyl-, aryl-, alkenyl- or other multiple unsaturated compounds. The conjugation between the variant polypeptide and the lipophilic compound, optionally through a linker may be done according to methods known in the art, e.g. as described by Bodanszky in Peptide Synthesis, John Wiley, New York, 1976 and in WO 96/12505.

Methods of Preparing a Polypeptide Variant of the Invention

The polypeptide variant of the present invention may be produced by any suitable method known in the art. Such methods include constructing a nucleotide sequence encoding the polypeptide variant and expressing the sequence in a suitable transformed or transfected host. Preferably, the host cell is a gammacarboxylating host cell such as a mammalian cell. However, polypeptide variants of the invention may be produced, albeit less efficiently, by chemical synthesis or a combination of chemical synthesis or a combination of chemical synthesis and recombinant DNA technology.

A nucleotide sequence encoding a polypeptide of the invention may be constructed by isolating or synthesizing a nucleotide sequence encoding the parent FVII, such as hFVII with the amino acid sequence shown in SEQ ID NO:2 and then changing the nucleotide sequence so as to effect introduction (i.e. insertion or substitution) or removal (i.e. deletion or substitution) of the relevant amino acid residue(s).

The nucleotide sequence is conveniently modified by site-directed mutagenesis in accordance with conventional methods. Alternatively, the nucleotide sequence is prepared by chemical synthesis, e.g. by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction (LCR) (Barany, PNAS 88:189-193, 1991). The individual oligonucleotides typically contain 5' or 3' overhangs for complementary assembly.

Alternative nucleotide sequence modification methods are available for producing polypeptide variants for high throughput screening, for instance methods which involve homologous cross-over such as disclosed in U.S. Pat. No. 5,093,257, and methods which involve gene shuffling, i.e. recombination between two or more homologous nucleotide sequences resulting in new nucleotide sequences having a number of nucleotide alterations when compared to the starting nucleotide sequences. Gene shuffling (also known as DNA shuffling) involves one or more cycles of random fragmentation and reassembly of the nucleotide sequences, followed by screening to select nucleotide sequences encoding polypeptides with desired properties. In order for homology-based nucleic acid shuffling to take place, the relevant parts of the nucleotide sequences are preferably at least 50% identical, such as at least 60% identical, more preferably at least 70% identical, such as at least 80% identical. The recombination can be performed in vitro or in vivo.

Examples of suitable in vitro gene shuffling methods are disclosed by Stemmer et al. (1994), Proc. Natl. Acad. Sci. USA; vol. 91, pp. 10747-10751; Stemmer (1994), Nature, vol. 370, pp. 389-391; Smith (1994), Nature vol. 370, pp. 324-325; Zhao et al., Nat. Biotechnol. 1998, March; 16(3): 258-61; Zhao H. and Arnold, F B, Nucleic Acids Research, 1997, Vol. 25. No. 6 pp. 1307-1308; Shao et al., Nucleic Acids Research 1998, Jan 15; 26(2): pp. 681-83; and WO 95/17413.

An example of a suitable in vivo shuffling method is disclosed in WO 97/07205. Other techniques for mutagenesis of nucleic acid sequences by in vitro or in vivo recombination are disclosed e.g. in WO 97/20078 and U.S. Pat. No. 5,837,458. Examples of specific shuffling techniques include "family shuffling", "synthetic shuffling" and "in silica shuffling".

Family shuffling involves subjecting a family of homologous genes from different species to one or more cycles of shuffling and subsequent screening or selection. Family shuffling techniques are disclosed e.g. by Crameri et al. (1998), Nature, vol. 391, pp. 288-291; Christians et al. (1999), Nature Biotechnology, vol. 17, pp. 259-264; Chang et al. (1999), Nature Biotechnology, vol. 17, pp. 793-797; and Ness et al (1999), Nature Biotechnology, vol. 17, 893-896.

Synthetic shuffling involves providing libraries of overlapping synthetic oligonucleotides based e.g. on a sequence alignment of homologous genes of interest. The synthetically generated oligonucleotides are recombined, and the resulting recombinant nucleic acid sequences are screened and if desired used for further shuffling cycles. Synthetic shuffling techniques are disclosed in WO 00/42561.

In silica shuffling refers to a DNA shuffling procedure, which is performed or to modelled using a computer system, thereby partly or entirely avoiding the need for physically manipulating nucleic acids. Techniques for in silico shuffling are disclosed in WO 00/42560.

Once assembled (by synthesis, site-directed mutagenesis or another method), the nucleotide sequence encoding the polypeptide is inserted into a recombinant vector and operably linked to control sequences necessary for expression of the FVII in the desired transformed host cell.

It should of course be understood that not all vectors and expression control sequences function equally well to express the nucleotide sequence encoding the polypeptide variants described herein. Neither will all hosts function equally well with the same expression system. However, one of skill in the art may make a selection among these vectors, expression control sequences and hosts without undue experimentation. For example, in selecting a vector, the host must be considered because the vector must replicate in it or be able to integrate into the chromosome. The vector's copy number, the ability to control that copy number, and the expression of any other proteins encoded by the vector, such as antibiotic markers, should also be considered. In selecting an expression control sequence, a variety of factors should also be considered. These include, for example, the relative strength of the sequence, its controllability, and its compatibility with the nucleotide sequence encoding the polypeptide, particularly as regards potential secondary structures. Hosts should be selected by consideration of their compatibility with the chosen vector, the toxicity of the product coded for by the nucleotide sequence, their secretion characteristics, their ability to fold the polypeptide variant correctly, their fermentation or culture requirements, and the ease of purification of the products coded for by the nucleotide sequence.

The recombinant vector may be an autonomously replicating vector, i.e. a vector, which exists as an extrachromosomal entity, the replication of which is independent of chromosomal replication, e.g. a plasmid. Alternatively, the vector is one which, when introduced into a host cell, is integrated into the host cell genome and replicated together with the chromosome(s) into which it has been integrated.

The vector is preferably an expression vector, in which the nucleotide sequence encoding the polypeptide variant of the invention is operably linked to additional segments required for transcription of the nucleotide sequence. The vector is typically derived from plasmid or viral DNA. A number of suitable expression vectors for expression in the host cells mentioned herein are commercially available or described in the literature. Useful expression vectors for eukaryotic hosts, include, for example, vectors comprising expression control sequences from SV40, bovine papilloma virus, adenovirus and cytomegalovirus. Specific vectors are, e.g., pcDNA3.1 (+)/Hyg (Invitrogen, Carlsbad, Calif., USA) and pCI-neo (Stratagene, La Jola, Calif., USA). Useful expression vectors for yeast cells include the 2µ plasmid and derivatives thereof, the POT1 vector (U.S. Pat. No. 4,931,373), the pJSO37 vector described in Okkels, Ann. New York Acad. Sci. 782, 202-207, 1996, and pPICZ A, B or C (Invitrogen). Useful vectors for insect cells include pVL941, pBG311 (Cate et al., "Isolation of the Bovine and Human Genes for Mullerian Inhibiting Substance And Expression of the Human Gene In Animal Cells", Cell, 45, pp. 685-98 (1986), pBluebac 4.5 and pMelbac (both available from Invitrogen). Useful expression vectors for bacterial hosts include known bacterial plasmids, such as plasmids from *E. coli*, including pBR322, pET3a and pET12a (both from Novagen Inc., WI, USA), wider host range plasmids, such as RP4, phage DNAs, e.g., the numerous derivatives of phage lambda, e.g., NM989, and other DNA phages, such as M13 and filamentous single stranded DNA phages.

Other vectors for use in this invention include those that allow the nucleotide sequence encoding the polypeptide variant to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction Of A Modular Dihydrofolate Reductase cDNA Gene: Analysis Of Signals Utilized For Efficient Expression", Mol. Cell. Biol., 2, pp. 1304-19 (1982)) and glutamine synthetase ("GS") amplification (see, e.g., U.S. Pat. No. 5,122,464 and EP 338,841).

The recombinant vector may further comprise a DNA sequence enabling the vector to replicate in the host cell in question. An example of such a sequence (when the host cell is a mammalian cell) is the SV40 origin of replication. When the host cell is a yeast cell, suitable sequences enabling the vector to replicate are the yeast plasmid 2µ replication genes REP 1-3 and origin of replication.

The vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 1985, pp. 125-130), or one which confers resistance to a drug, e.g. ampicillin, kanamycin, tetracyclin, chloramphenicol, neomycin, hygromycin or methotrexate. For *Saccharomyces cerevisiae*, selectable markers include ura3 and leu2. For filamentous fungi, selectable markers include amdS, pyrG, arcB, niaD and sC.

The term "control sequences" is defined herein to include all components, which are necessary or advantageous for the expression of the polypeptide variant of the invention. Each control sequence may be native or foreign to the nucleic acid sequence encoding the polypeptide variant. Such control sequences include, but are not limited to, a leader sequence, polyadenylation sequence, propeptide sequence, promoter, enhancer or upstream activating sequence, signal peptide sequence, and transcription terminator. At a minimum, the control sequences include a promoter.

A wide variety of expression control sequences may be used in the present invention. Such useful expression control sequences include the expression control sequences associated with structural genes of the foregoing expression vectors as well as any sequence known to control the expression of genes of prokaryotic or eukaryotic cells or their viruses, and various combinations thereof.

Examples of suitable control sequences for directing transcription in mammalian cells include the early and late promoters of SV40 and adenovirus, e.g. the adenovirus 2 major late promoter, the MT-1 (metallothionein gene) promoter, the human cytomegalovirus immediate-early gene promoter (CMV), the human elongation factor 1α (EF-1α) promoter, the *Drosophila* minimal heat shock protein 70 promoter, the Rous Sarcoma Virus (RSV) promoter, the human ubiquitin C (UbC) promote; the human growth hormone terminator, SV40 or adenovirus E1b region polyadenylation signals and the Kozak consensus sequence (Kozak, M. *J Mol Biol* 1987 Aug. 20; 196(4):947-50).

In order to improve expression in mammalian cells a synthetic intron may be inserted in the 5' untranslated region of the nucleotide sequence encoding the polypeptide. An example of a synthetic intron is the synthetic intron from the plasmid pCI-Neo (available from Promega. Corporation, WI, USA).

Examples of suitable control sequences for directing transcription in insect cells include the polyhedrin promoter, the P10 promoter, the *Autographa californica* polyhedrosis virus basic protein promoter, the baculovirus immediate early gene 1 promoter and the baculovirus 39K delayed-early gene promoter, and the SV40 polyadenylation sequence. Examples of suitable control sequences for use in yeast host cells include the promoters of the yeast α-mating system, the yeast triose phosphate isomerase (TPI) promoter, promoters from yeast glycolytic genes or alcohol dehydrogenase genes, the ADH2-4-c promoter, and the inducible GAL promoter. Examples of suitable control sequences for use in filamentous fungal host cells include the ADH3 promoter and terminator, a promoter derived from the genes encoding *Aspergillus oryzae* TAKA amylase triose phosphate isomerase or alkaline protease, an

*A. niger* α-amylase, *A. niger* or *A. nidulans* glucoamylase, *A. nidulans* acetamidase, *Rhizomucor miehei* aspartic proteinase or lipase, the TPI1 terminator and the ADH3 terminator. Examples of suitable control sequences for use in bacterial host cells include promoters of the lac system, the trp system, the TAC or TRC system, and the major promoter regions of phage lambda.

The presence or absence of a signal peptide will, e.g., depend on the expression host is cell used for the production of the polypeptide variant to be expressed (whether it is an intracellular or extracellular polypeptide) and whether it is desirable to obtain secretion. For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase. For use in insect cells, the signal peptide may conveniently be derived from an insect gene (of WO 90/05783), such as the *Lepidopteran manduca sexta* adipokinetic hormone precursor, (cf. U.S. Pat. No. 5,023,328), the honeybee melittin (Invitrogen), ecdysteroid UDPglucosyltransferase (egt) (Murphy et al., Protein Expression and Purification 4, 349-357 (1993) or human pancreatic lipase (hp1) (Methods in Enzymology 284, pp. 262-272, 1997). A preferred signal peptide for use in mammalian cells is that of hPVII or the murine Ig kappa light chain signal peptide (Coloma, M (1992) J. Imm. Methods 152:89404). For use in yeast cells suitable signal peptides have been found to be the α-factor signal peptide from *S. cereviciae* (cf. U.S. Pat. No. 4,870,008), a modified carboxypeptidase signal peptide (cf. L. A. Valls et al., Cell 48, 1987, pp. 887-897), the yeast BART signal peptide (cf. WO 87/02670), the yeast aspartic protease 3 (YAP3) signal peptide (cf. M. Egel-Mitani et al., Yeast 6, 1990, pp. 127-137), and the synthetic leader sequence TA57 (WO98/32867). For use in *E. coli* cells a suitable signal peptide have been found to be the signal peptide ompA (EP581821).

The nucleotide sequence of the invention encoding a polypeptide variant, whether prepared by site-directed mutagenesis, synthesis, PCR or other methods, may optionally include a nucleotide sequence that encode a signal peptide. The signal peptide is present when the polypeptide variant is to be secreted from the cells in which it is expressed. Such signal peptide, if present, should be one recognized by the cell chosen for expression of the polypeptide variant. The signal peptide may, e.g. be that normally associated with hFVII) or, alternatively, the signal peptide may be from another source than hFVII, such as any of those normally associated with other human wild-type vitamin K-dependent polypeptides. Furthermore, the signal peptide may be a signal peptide normally expressed from the host cell or one which is not normally expressed from the host cell. Accordingly, the signal peptide may be prokaryotic, e.g. derived from a bacterium such as *E. coli*, or eukaryotic, e.g. derived from a mammalian, or insect or yeast cell.

Any suitable host may be used to produce the polypeptide variant, including bacteria (although not particularly preferred), fungi (including yeasts), plant, insect, mammal, or other appropriate animal cells or cell lines, as well as transgenic animals or plants. Examples of bacterial host cells include grampositive bacteria such as strains of *Bacillus*, e.g. *B. brevis* or *B. subtilis*, *Pseudomonas* or *Streptomyces*, or gramnegative bacteria, such as strains of *E. coli*. The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278). Examples of suitable filamentous fungal host cells include strains of *Aspergillus*, e.g. *A. oryzae*, *A. niger*, or *A. nidulans*, *Fusarium* or *Trichoderma*. Fungal cells may be transformed by a process involving protoplast formation, transformation of the protoplasts, and regeneration of the cell wall in a manner known per se. Suitable procedures for transformation of *Aspergillus* host cells are described in EP 238 023 and U.S. Pat. No. 5,679,543. Suitable methods for transforming *Fusarium* species are described by Malardier et al., 1989, *Gene* 78: 147-156 and WO 96/00787. Examples of suitable yeast host cells include strains of *Saccharomyces*, e.g. *S. cerevisiae*, *Schizosaccharomyces*, *Klyveromyces*, *Pichia*, such as *P. pastoris* or *P. methanolica*, *Hansenula*, such as *H. Polymorpha* or *Yarrowia*. Yeast may be transformed using the procedures described by Becker and Guarente, In Abelson, S. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; Hinnen et al., 1978, *Proceedings of the National Academy of Sciences USA* 75: 1920: and as disclosed by Clontech Laboratories, Inc, Palo Alto, Calif., USA (in the product protocol for the Yeastmaker™ Yeast Transformation System Kit). Examples of suitable insect host cells include a *Lepidoptora* cell line, such as *Spodoptera frugiperda* (SD or S121) or *Trichoplusioa ni* cells (High Five) (U.S. Pat. No. 5,077,214). Transformation of insect cells and production of heterologous polypeptides therein may be performed as described by Invitrogen. Examples of suitable mammalian host cells include Chinese hamster ovary (CHO) cell lines, (e.g. CHO-K1; ATCC CCL-61), Green Monkey cell lines (COS) (e.g. COS 1 (ATCC CRL-1650), COS 7 (ATCC CRL-1651)); mouse cells (e.g. NS/O), Baby Hamster Kidney (31-1K) cell lines (e.g. ATCC CRL-1632 or ATCC CCL-10), and human cells (e.g. HEK 293 (ATCC CRL-1573)), as well as plant cells in tissue culture. Additional suitable cell lines are known in the art and available from public depositories such as the American Type Culture Collection, Rockville, Md. Also, the mammalian cell, such as a CHO cell, may be modified to express sialyltransferase, e.g. 1,6-sialyltransferase, e.g. as described in U.S. Pat. No. 5,047,335, in order to provide improved glycosylation of the polypeptide variant.

In order to increase secretion it may be of particular interest to produce the polypeptide variant of the invention together with an endoprotease, in particular a PACE (paired basic amino acid converting enzyme) (e.g. as described in U.S. Pat. No. 5,986,079), such as a Kex2 endoprotease (e.g. as described in WO 00/28065).

Methods for introducing exogenous DNA into mammalian host cells include calcium phosphate-mediated transfection, electroporation, DEAE-dextran mediated transfection, liposome-mediated transfection, viral vectors and the transfection method described by Life Technologies Ltd, Paisley, UK using Lipofectamin 2000. These methods are well known in the art and e.g. described by Ausbel et al. (eds.), 1996, Current Protocols in Molecular Biology, John Wiley & Sons, New York, USA. The cultivation of mammalian cells are conducted according to established methods, e.g. as disclosed in (Animal Cell Biotechnology, Methods and Protocols, Edited by Nigel Jenkins, 1999, Human Press Inc, Totowa, N.J., USA and Harrison M A and Rae I F, General Techniques of Cell Culture, Cambridge University Press 1997).

In the production methods of the present invention, the cells are cultivated in a nutrient medium suitable for production of the polypeptide variant using methods known in the art. For example, the cell may be cultivated by shake flask cultivation, small-scale or large-scale fermentation (including continuous, batch, fed batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide variant is secreted into the nutrient medium, the polypeptide can be recovered directly from the medium. Tithe polypeptide variant is not secreted, it can be recovered from cell lysates.

The resulting polypeptide variant may be recovered by methods known in the art. For example, the polypeptide variant may be recovered from the nutrient medium by conventional procedures including, but not limited to, centrifugation, filtration, extraction, spray drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), HPLC, or extraction (see, e.g., *Protein Purification*, J.-C. Janson and Lars Ryden, editors, VCH Publishers, New York, 1989).

Single chain polypeptide variants of the invention can be purified and activated to two-chain polypeptide variants by a number of methods as described in the literature (Broze and Majerus, 1980, J. Biol. Chem. 255:1242-47 and Hedner and Kisiel, 1983, J. Clin. Invest. 71:1836-41). Another method whereby single chain polypeptide variant can be purified is by incorporation of Zn ions during purification as described in U.S. Pat. No. 5,700,914. In a preferred embodiment the polypeptide variant is purified as a single chain polypeptide variant. The single chain polypeptide variant is activated by either use of an immobilized enzyme (e.g. factors IIa, IXa, Xa and XIIa) or by autoactivation using a positively charged ion exchange matrix or the like.

It is advantageous to first purify the polypeptide variant in its single chain form, then PEGylate (if desired) and last activate by one of the methods described above or by autoactivation as described by Pedersen et al, 1989, Biochemistry 28: 9331-36. The advantage of carrying out PEGylation before activation is that PEGylation of the new aminoterminal formed by cleavage of R152-I153 is avoided. PEGylation of this new amino terminal would render the molecule inactive since the formation of a hydrogen bond between D242 and the amino terminal of I153 is necessary for activity.

Pharmaceutical Composition of the Invention and its Use

In a further aspect, the present invention relates to a composition, in particular to a pharmaceutical composition, comprising a polypeptide variant of the invention and a pharmaceutically acceptable carrier or excipient.

The polypeptide variant or the pharmaceutical composition according to the invention may be used as a medicament.

Due to the improved properties mentioned hereinbefore, the polypeptide variants of the invention, or the pharmaceutical composition of the invention, are particular useful for the treatment of uncontrollable bleeding events in trauma patients, thrombocytopenic patients, patients in anticoagulant treatment, and cirrhosis patients with variceal bleeds, or other upper gastrointestinal bleedings, and in patients undergoing orthotopic liver transplantation, or liver resection (allowing for transfusion free surgery).

Trauma is defined as an injury to living tissue caused by an extrinsic agent. It is the $4^{th}$ leading cause of death in the US and places a large financial burden on the economy.

Trauma is classified as either blunt or penetrative. Blunt trauma results in internal compression, organ damage and internal haemorrhage whereas penetrative trauma (as the consequence of an agent penetrating the body and destroying tissue, vessels and organs) results in external haemorrhage.

Haemorrhage, as a result of trauma, can start a cascade of problems. For example physiological compensation mechanisms are initiated with initial peripheral and mesenteric vasoconstriction to shunt blood to the central circulation. If circulation is not restored, hypovolemia shock (multiple organ failure due to inadequate perfusion) ensues. Since tissues throughout the body become starved for oxygen, anaerobic metabolism begins. However, the concomitant lactic acid leads the blood pH to drop and metabolic acidosis develops. If acidosis is severe and uncorrected, the patient may develop multisystem failure and die.

Although the majority of trauma patients are hypothermic on arrival in the emergency room due to the environmental conditions at the scene, inadequate protection, intravenous fluid administration and ongoing blood loss worsen the hypothermic state. Deficiencies in coagulation factors can result from blood loss or transfusions. Meanwhile, acidosis and hypothermia interfere with blood clotting mechanisms. Thus coagulopathy develops, which in turn, may mask surgical bleeding sites and hamper the control of mechanical bleeding. Hypothermia, coagulopathy and acidosis are often characterised as the "trauma triad of death"

Trauma may be caused by several events. For example, road traffic accidents result in many different types of trauma. Whilst some road traffic accidents are likely to result in penetrative trauma, many road traffic accidents are likely to inflict blunt trauma to both head and body. However, these various types of trauma can all result in coagulopathy in the patient. Road traffic accidents are the leading cause of accidental death in the US. There are over 42,000 deaths from them in the US each year. Many trauma patients die at the location of the accident either whilst being treated by the paramedics, before they arrive or in transit to the ER.

Another example includes gunshot wounds. Gunshot wounds are traumas that can result in massive bleeding. They are penetrative and destroy tissue as the bullet passes through to the body, whether it be in the torso or a limb. In the US about 40,000 people a year die from gunshot wounds A further example includes falls. Falls result in a similar profile of trauma type to road traffic accidents. By Oiling onto a solid object or the ground from height can cause both penetrative and decelerative blunt trauma. In the US, falls are a common cause of accidental death, numbering about 13,000.

A still further example includes machinery accidents. A smaller number of people die in the US from machinery accident related deaths, whether struck by, or entangled in machinery. The figures are small but significant—around 2,000.

A still further example includes stab wounds. Stab wounds are penetrative injuries that can also cause massive bleeding. The organs most likely to be damaged in a stab wound are the liver, small intestine and the colon.

Cirrhosis of the liver is the terminal sequel of prolonged repeated injury to the hepatic parenchyma. The end result is the formation of broad bands of fibrous tissue separating regenerative nodules that do not maintain the normal organization of liver lobules and thus cause deteriorated liver function. Patients have prolonged prothrombin times as a result of the depletion of vitamin K-dependent coagulation factors. Pathogenetically, liver cirrhosis should be regarded as the final common pathway of chronic liver injury, which can result from any form of intense repeated prolonged liver cell injury. Cirrhosis of the liver may be caused by direct liver injury, including chronic alcoholism, chronic viral hepatitis (types B, C, and D), and auto immune hepatitis as well as by indirect injury by way of bile duct damage, including primary biliary cirrhosis, primary sclerosing cholangitis and biliary atresia. Less common causes of cirrhosis include direct liver injury from inherited disease such as cystic fibrosis, alpha-1-antitrypsin deficiency, hemochromatosis, Wilson's disease, galactosemia, and glycogen storage disease.

Transplantation is primarily reserved for late stage cirrhotic patients, where it is the key intervention for treating the disease. To be eligible for transplantation, a patient must be classified as Child's B or C, as well as meet additional criteria for selection. Last year, in the US alone, 4,954 transplants were performed.

It has been estimated that there are 6,000 bleeding episodes associated with patients undergoing resection each year. This correlates with the reserved position of this procedure although seems slightly high in comparison with transplantation numbers.

Accurate data on the incidence of variceal bleeding is hard to obtain. The key facts known are that at the time of diagnosis, varices are present in about 60% of decompensated and 30% of compensated patients and that about 30% of these patients with varices will experience a bleed and that each episode of variceal bleeding is associated with a 30% risk of mortality.

Thus, in a further aspect the present invention relates to a polypeptide variant of the invention for the manufacture of a medicament for the treatment of diseases or disorder wherein clot formation is desirable. A still further aspect of the present invention relates to a method for is treating a mammal having a disease or disorder wherein clot formation is desirable, comprising administering to a mammal in need thereof an effective amount of the polypeptide variant or the pharmaceutical composition of the invention.

Thrombocytopenia is caused by one of three mechanisms-decreased bone marrow production, increased splenic sequestration, or accelerated destruction of platelets. Thrombocytopenia is a risk factor for hemorrhage, and platelet transfusion reduces the incidence of bleeding. The threshold for prophylactic platelet transfusion is 10,000/µl. In patients without fever or infections, a threshold of 5000/µl may be sufficient to prevent spontaneous hemorrhage. For invasive procedures, 50,000/µl platelets is the usual target level. In patients who develop antibodies to platelets following repeated transfusions, bleeding can be extremely difficult to control.

Examples of diseases/disorders wherein increased clot formation is desirable include, but is not limited to, hemorrhages, including brain hemorrhages, as well as patient with severe uncontrolled bleedings, such as trauma. Further examples include patients undergoing living transplantations, patients undergoing resection and patients with variceal bleedings.

The polypeptide variants of the invention is administered to patients in a therapeutically effective dose, normally one approximately paralleling that employed in therapy with rFVII such as NovoSeven®, or at lower dosage. By "therapeutically effective dose" herein is meant a dose that is sufficient to produce the desired effects in relation to the condition for which it is administered. The exact dose will depend on the circumstances, and will be ascertainable by one skilled in the art using known techniques. Normally, the dose should be capable of preventing or lessening the severity or spread of the condition or indication being treated. It will be apparent to those of skill in the art that an effective amount of a polypeptide variant or composition of the invention depends, inter alia, upon the disease, the dose, the administration schedule, whether the polypeptide variant or composition is administered alone or in conjunction with other therapeutic agents, the plasma half-life of the compositions, and the general health of the patient. Preferably, the polypeptide variant or composition of the invention is administered in an effective dose, in particular a dose which is sufficient to normalize the to coagulation disorder.

The polypeptide variant of the invention is preferably administered in a composition including a pharmaceutically acceptable carrier or excipient "Pharmaceutically acceptable" means a carrier or excipient that does not cause any untoward effects in patients to whom it is administered. Such pharmaceutically acceptable carriers and excipients are well known in the art (see, for example, Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]).

The polypeptide variant of the invention can be formulated into pharmaceutical compositions by well-known methods. Suitable formulations are described by Remington's Pharmaceutical Sciences by E. W. Martin (Mark Publ. Co., 16th Ed., 1980).

The polypeptide variant of the invention can be used "as is" and/or in a salt form thereof. Suitable salts include, but are not limited to, salts with alkali metals or alkaline earth metals, such as sodium, potassium, calcium and magnesium, as well as e.g. zinc salts. These salts or complexes may by present as a crystalline and/or amorphous structure.

The pharmaceutical composition of the invention may be administered alone or in conjunction with other therapeutic agents. These agents may be incorporated as part of the same pharmaceutical composition or may be administered separately from the polypeptide variant of the invention, either concurrently or in accordance with another treatment schedule. In addition, the polypeptide variant or pharmaceutical composition of the invention may be used as an adjuvant to other therapies.

A "patient" for the purposes of the present invention includes both humans and other mammals. Thus, the methods are applicable to both human therapy and veterinary applications. The pharmaceutical composition comprising the polypeptide variant of the invention may be formulated in a variety of forms, e.g. as a liquid, gel, lyophilized, or as a compressed solid. The preferred form will depend upon the particular indication being treated and will be apparent to one skilled in the art.

In particular, the pharmaceutical composition comprising the polypeptide variant of the invention may be formulated in lyophilised or stable soluble form. The polypeptide variant may be lyophilized by a variety of procedures known in the art. The polypeptide variant may be in a stable soluble form by the removal or shielding of proteolytic degradation sites as described herein. The advantage of obtaining a stable soluble preparation lies in easier handling for the patient and, in the case of emergencies, quicker action, which potentially can become life saving. The preferred form will depend upon the particular indication being treated and will be apparent to one of skill in the art.

The administration of the formulations of the present invention can be performed in a variety of ways, including, but not limited to, orally, subcutaneously, intravenously, intracerebrally, intranasally, transdermally, intraperitoneally, intramuscularly, intrapulmonary, vaginally, rectally, intraocularly, or in any other acceptable manner. The formulations can be administered continuously by infusion, although bolus injection is acceptable, using techniques well known in the art, such as pumps or implantation. In some instances the formulations may be directly applied as a solution or spray.

Parentals

A preferred example of a pharmaceutical composition is a solution designed for parenteral administration. Although in many cases pharmaceutical solution formulations are provided in liquid form, appropriate for immediate use, such parenteral formulations may also be provided in frozen or in lyophilized form. In the former case, the composition must be thawed prior to use. The latter form is often used to enhance the stability of the active compound contained in the composition under a wider variety of storage conditions, as it is recognized by those skilled in the art that lyophilized preparations are generally more stable than their liquid counterparts. Such lyophilized preparations are reconstituted prior to use by the addition of one or more suitable pharmaceutically acceptable diluents such as sterile water for injection or sterile physiological saline solution.

In case of parenterals, they are prepared for storage as lyophilized formulations or aqueous solutions by mixing, as appropriate, the polypeptide variant having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic surfactants or detergents, antioxidants and/or other miscellaneous additives.

Buffering agents help to maintain the pH in the range which approximates physiological conditions. They are typically present at a concentration ranging from about 2 mM to about 50 mM. Suitable buffering agents for use in the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium gly-uconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, histidine buffers and trimethylamine salts such as Tris.

Stabilizers refer to a broad category of excipients, which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, $\alpha$-monothioglycerol and sodium thiosulfate; low molecular weight polypeptides (i.e. <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on the active protein weight.

Preservatives are added to retard microbial growth, and are typically added in amounts of about 0.2%-1% (w/v). Suitable preservatives for use with the present invention include phenol, benzyl alcohol, meta-cresol, methyl paraben, propyl paraben, octadecyldimethylbenzyl ammonium chloride, benzalkonium halides (e.g. benzalkonium chloride, bromide or iodide), hexamethonium chloride, alkyl parabens such as methyl or propyl paraben, catechol, resorcinol, cyclohexanol and 3-pentanol.

Isotonicifiers are added to ensure isotonicity of liquid compositions and include to polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Non-ionic surfactants or detergents (also known as "wetting agents") may be present to help solubilizing the therapeutic agent as well as to protect the therapeutic polypeptide against agitation-induced aggregation, which also permits the formulation to be exposed to shear surface stress without causing denaturation of the polypeptide. Suitable non-ionic surfactants include polysorbates (20, 80, etc.), polyoxamers (184, 188 etc.), Pluronic® polyols, polyoxyethylene sorbitan monoethers (TWEEN®-20(polyoxyethylenesorbitan monolaurate), TWEEN®-80 (polyoxyethylenesorbitan monooleate, etc.).

Additional miscellaneous excipients include bulking agents or fillers (e.g. starch), chelating agents (e.g. EDTA), antioxidants (e.g., ascorbic acid, methionine, vitamin E) and cosolvents.

The active ingredient may also be entrapped in microcapsules prepared, for example, by coascervation techniques or by interfacial polymerization, for example hydroxymethylcellulose, gelatin or poly-(methylmethacylate) microcapsules, in colloidal drug delivery systems (for example liposomes, albumin microspheres, microemulsions, nanoparticles and nanocapsules) or in macroemulsions. Such techniques are disclosed in Remington's Pharmaceutical Sciences, supra.

Parenteral formulations to be used for in vivo administration must be sterile. This is readily accomplished, for example, by filtration through sterile filtration membranes.

Sustained Release Preparations

Examples of sustained-release preparations include semipermeable matrices of solid hydrophobic polymers containing the polypeptide variant, the matrices having a suitable form such as a film or microcapsules. Examples of sustained-release matrices include polyesters, hydrogels-(for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as the Pro-Lease® technology or Lupron Depot® (injectable microspheres composed of lactic acid-glycolic acid copolymer and leuprolide acetate), and poly-D-(−)-5-hydroxybutyric acid. While polymers such to as ethylene-vinyl acetate and lactic acid-glycolic acid enable release of molecules for long periods such as up to or over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The invention is further described in the following non-limiting examples.

Materials and Methods

Accessible Surface Area (ASA)

The computer program Access (B. Lee and F. M. Richards, J. Mol. Biol. 55: 379-400 (1971)) version 2 (© 1983 Yale University) is used to compute the accessible surface area (ASA) of the individual atoms in the structure. This method typically uses a probe-size of 1.4 Å and defines the Accessible Surface Area (ASA) as the area formed by the center of the probe. Prior to this calculation all water molecules and all hydrogen atoms should be removed from the coordinate set, as should other atoms not directly related to the protein.

Fractional ASA of Side Chain

The fractional ASA of the side chain atoms is computed by division of the sum of the ASA of the atoms in the side chain with a value representing the ASA of the side chain atoms of that residue type in an extended Ala-x-Ma tripeptide (See Hubbard, Campbell & Thornton (1991) J. Mol. Biol. 220, 507-530). For this example the CA atom is regarded as a part of the side chain of Glycine residues but not for the remaining residues. The following table is used as standard 100% ASA for the side chain:

| | |
|---|---|
| Ala | 69.23 Å$^2$ |
| Arg | 200.35 Å$^2$ |
| Asn | 106.25 Å$^2$ |
| Asp | 102.06 Å$^2$ |
| Cys | 96.69 Å$^2$ |
| Gln | 140.58 Å$^2$ |
| Glu | 134.61 Å$^2$ |
| Gly | 32.28 Å$^2$ |
| His | 147.00 Å$^2$ |
| Ile | 137.91 Å$^2$ |
| Leu | 140.76 Å$^2$ |
| Lys | 162.50 Å$^2$ |
| Met | 156.08 Å$^2$ |
| Phe | 163.90 Å$^2$ |
| Pro | 119.65 Å$^2$ |
| Ser | 78.16 Å$^2$ |
| Thr | 101.67 Å$^2$ |
| Trp | 210.89 Å$^2$ |
| Tyr | 176.61 Å$^2$ |
| Val | 114.14 Å$^2$ |

Residues not detected in the structure are defined as having 100% exposure as they are thought to reside in flexible regions. The gamma-carboxy glutamic acids at positions 6, 7, 14, 16, 19, 20, 25, 26, 29 and 35 are all defined as being 100% exposed.

Determining Distances Between Atoms

The distance between atoms is most easily determined using molecular graphics software e.g. InsightII® v.98.0, MSI INC.

Active Site Region

The active site region is defined as any residues having at least one atom within 10 Å of any atom in the catalytic triad (residues H193, D242, S344).

Determination of Tissue Factor Binding Site

The TF binding site is defined as comprising of all residues having their accessible surface area changed upon TF binding. This is determined by at least two ASA calculations; one on the isolated ligand(s) in the ligand(s)/receptor(s) complex and one on the complete ligand(s)/receptor(s) complex.

Measurement of Reduced Sensitivity to Proteolytic Degradation

Proteolytic degradation can be measured using the assay described in U.S. Pat. No. 5,580,560, Example 5, where proteolysis is autoproteolysis.

Furthermore, reduced proteolysis can be tested in an in vivo model using radiolabelled samples and comparing proteolysis of rhFVIIa and the polypeptide variant of the invention by withdrawing blood samples and subjecting these to SDS-PAGE and autoradiography.

Irrespectively of the assay used for determining proteolytic degradation, "reduced proteolytic degradation" is intended to mean a measurable reduction in cleavage compared to that obtained by rhFVIIa as measured by gel scanning of Coomassie stained SDS-PAGE gels, HPLC or as measured by conserved catalytic activity in comparison to wild type using the tissue factor independent activity assay described below.

Determination of the Molecular Weight of Polypeptide Variants

The molecular weight of polypeptide variants is determined by either SOS-PAGE, gel filtration, Western Blots, matrix assisted laser desorption mass spectrometry or equilibrium centrifugation, e.g. SDS PAGE according to Laemmli, U.K., Nature Vol 227 (1970), pp. 680-85.

TF-Independent Factor X Activation Assay

This assay has been described in detail on page 39826 in Nelsestuen et al., J. Biol Chem, 2001; 276:39825-39831.

Briefly, the molecule to be assayed (either hFVIIa, rhFVIIa or the polypeptide variant of the invention in its activated form) is mixed with a source of phospholipid (phosphatidylcholine and phosphatidylserine in a ratio of 8:2 or phosphatidylcholine, phosphatidylserine and phosphatidylethanol in a ratio of 4:2:4) and Factor X in Tris buffer containing BSA. After a specified incubation time the reaction is stopped by addition of excess EDTA. The concentration of factor Xa is then measured from absorbance change at 405 nm after addition of a chromogenic substrate (S-2222, Chromogenix). After correction from background the tissue factor independent activity of rhFVIIa ($a_{wt}$) is determined as the absorbance change after 10 minutes and the tissue factor independent activity of the polypeptide variant of the invention ($a_{variant}$) is also determined as the absorbance change after 10 minutes. The ratio between the activity of the polypeptide variant, in its activated form, and the activity of rhFVIIa is defined as $a_{variant}/a_{wt}$.

Clotting Assay

Clotting activity is measured in one-stage assays and clotting times are recorded on a Thrombotrack IV coagulometer (MEDINOR). FVII depleted human plasma (American Diagnostica) is reconstituted and equilibrated at room temperature for 15-20 minutes. 50 µl of plasma is then transferred to the coagulometer cups.

hFVIIa, rhFVIIa or variants are diluted in Glyoxaline Buffer (5.7 mM barbiturate, 4.3 mM sodium citrate, 117 mM NaCl, 1 mg/mL BSA, pH 7.35). The samples are added to the cup in 50 µl and incubated at 37° C. for 2 minutes.

Thromboplastin (MEDINOR) is reconstituted with water and $CaCl_2$ is added. The reaction is initiated by adding 0.1 ml thromboplastin containing 4.5 mM $CaCl_2$.

Data are analysed using PRISM software.

TF Independent Clotting Assay

This assay is performed as described above under "Clotting Assay" but without addition of thromboplastin.

Amidolytic Assay

The ability of the variants to cleave small peptide substrates can be measured using the chromogenic substrate S-2288 (D-Ile-Pro-Arg-p-nitroanilide). The amidolytic activity may be measured both in the presence and absence of antithrombin BI (ATIII).

HFVIIa, rhFVIIa or variant is diluted to 90 nM in assay buffer (50 mM Na-Hepes pH 7.5, 150 mM NaCl, 5 mM $CaCl_2$, 0.1% BSA, 10 ml Heparin). Furthermore, soluble TF (sTF) is diluted to 450 nM in assay buffer. ATIII is diluted to 900 nM in assay buffer. 120 µl of assay buffer is mixed with 20 µl of the FVIIa sample, 20 µl sTF and 20 µl ATIII or assay buffer. The final concentrations of FVIIa, sTF and ATIII are 10, 50 and 100 nM, respectively. After 5 min incubation at room temperature with gentle shaking, followed by 10 rain incubation at 37° C., the reaction is started by addition of the S-2288 substrate to 1 mM and the absorption at 405 nm is determined at several time points.

Thrombogram Assay

The effect of hFVIIa, rhFVIIa or variant on thrombin generation in human plasma is tested in a modified version of the assay described on page 589 in Hanker et al. in Thromb Haemost 2000; 83: 589-91. Briefly, the molecule to be assayed (either hFVIIa, rhFVIIa or variant) is mixed with normal platelet rich plasma (PRP), normal platelet poor plasma (PPP) or FVII depleted PPP with or without the addition of recombinant human tissue factor (rTF), relipidated rTF or another source of TF (such as thromboplastin). A source of phospholipid (phosphatidylcholine and phosphatidylserine in a ratio of 8:2 or phosphatidylcholine, phosphatidylserine and phosphatidylethanol in a ratio of 4:2:4) can be added.

The reaction is started by addition of a fluoregenic thrombin substrate and calcium chloride. The fluorescence is measured continuously and the thrombin amidolytic activity is calculated by calculating the slope of the fluorescence curve (the increase in fluorescence over time). In this way the time until maximum thrombin amidolytic activity is obtained ($T_{max}$) and total thrombin work (area under the curve (AUC)) can be calculated.

The following procedure is used: PRP is obtained by centrifuging freshly drawn blood at 250 g, 15° C. for 10 min. Blood coagulation is inhibited either by using citrate (13 mM tri-sodium citrate), corn trypsin inhibitor (50-100 µg/ml blood) or a combination of citrate and corn trypsin inhibitor. The platelet count is adjusted to $3 \times 10^8$/mL using buffer or autologous platelet poor plasma (PPP). PPP is obtained by double centrifugation of PRP at 1000 g, 15° C. for 10 min. FVII depletion is done by incubating PPP with a FVII specific monoclonal antibody coupled to a solid phase.

Per well of a 96-well microliter plate 80 µl PRP is added and 20 µL buffer containing rhFVII or variant to be tested in final concentrations between 0.1 and 100 nM. rTF is added in 5 µl, assay buffer to a final concentration of 1 µM. The assay buffer consists of 20 mM Hepes, 150 mM NaCl and 60 mg/ml BSA in distilled water. The reaction is started by adding 20 µL of the substrate solution containing 0.1 M calcium chloride. The assay plate and reagents are prewarmed to 37° C. and the reaction takes place at this temperature. The fluorimeter used is a BMG Fluormeter with a excitation filter at 390 nm and an emission filter at 460 nm. The fluorescence is measured in each well of 96-well clear bottom plates in 20-40 second interval over 30-180 minutes. Data are analyzed using PRISM Software.

ELISA Assay

FVII/PVIIa (or variant) concentrations are determined by ELISA. Wells of a microtiter plate are coated with an antibody directed against the protease domain using a solution of 2 µg/ml in PBS (100 µl per well). After 2 hours coating at R.T., the wells are washed 4 times with THT buffer (100 mM NaCl, 50 mM Tris-HCl pH 7.2 0.05% TWEEN®-20 (polyoxyethylenesorbitan monolaurate)). Subsequently, 200 µl of 1% Casein (diluted from 2.5% stock using 100 mM NaCl, 50 mM Tris-HCl pH 7.2) is added per well for blocking. After 1 hr incubation at R.T., the wells are emptied, and 100 µl of sample (optionally diluted in dilution buffer (THT+0.1% Casein)) is added. After another incubation of 1 hr at room temperature, the wells are washed 4 times with THT buffer, and 100 µl of a biotin-labelled antibody directed against the EGF-like domain (1 µg/ml) is added. After another 1 hr incubation at RT., followed by 4 more washes with THT buffer, 100 µl of streptavidin-horse radish peroxidase (DAKO A/S, Glostrup, Denmark, 1/10000 diluted) is added. After another 1 hr incubation at R.T., followed by 4 more washes with THT buffer, 100 µl of TMB (3,3',5,5'-tetramethylbenzidine, Kemen-Tech A/S, Denmark) is added. After 30 min incubation at R.T. in the dark, 100 µl of 1 M $H_2SO_4$ is added and $OD_{450nm}$, is determined. A standard curve is prepared using rhFVIIa (NovoSeven®).

Alternatively, FVII/FVIIa or variants may be quantified through the Gla domain rather than through the protease domain. In this ELISA set-up, wells are coated overnight with an antibody directed against the EGF-like domain and for detection, a calcium-dependent biotin-labelled monoclonal anti-Gla domain antibody is used (2 µg/ml, 100 µl per well). In this set-up, 5 mM $CaCl_2$ is added to the THT and dilution buffers.

Whole Blood Assay

The whole blood clotting assay is performed as described by Big et al. Thrombosis Res. 2001, 101(3):159-170.

Reconstituted Coagulation Assay

The reconstituted coagulation assay is performed as described by Van't Veer et al. Blood 2000, 95(4), 1330-1335.

EXAMPLES

Example 1

The X-ray structure of hFVIIa in complex with soluble tissue factor by Banner et. al., J Mol Biol, 1§96; 285:2089 is used for this example. It is noted that the numbering of residues in the reference does not follow the sequence. Here we have used the sequential numbering according to SEQ ID NO:2. The gamma-carboxy glutamic acids at positions 6, 7, 14, 16, 19, 20, 25, 26, 29 and 35 are all here named GLU (three letter abbreviation) or E (one letter abbreviation). Residues 143-152 are not present in the structure.

Surface Exposure

Performing fractional ASA calculations on FVII fragments alone combined with the definition of accessibilities of non standard and/or missing residues described in the methods resulted in the following residues having more than 25% of their side chain exposed to the surface: A1, N2, A3, F4, L5, E6, E7, L8, R9, P10, S12, L13, E14, E16, K18, E19, E20, Q21, S23, F24, E25, E26, R28, E29, F31, K32, D33, A34, E35, R36, K38, L39, W41, I42, S43, S45, G47, D48, Q49, A51, 852, S53, Q56, G58, 560, K62, I363, Q64, L65, Q66, 567, I69, F71, L73, P74, A75, E77, G78, R79, E82, T83, H84, K85, D86, D87, Q88, L89, I90, V92, N93, E94, G97, E99, S103, D104, H105, T106, G107, T108, K109, S111, R113, E116, G117, S119, L120, L121, A122, D123, G124, V125, 5126, T128, P129, T130, V131, E132, I140, L141, E142, K143, R144, N145, A146, S147, K148, P149, Q150, G151, R152, G155, K157, V158, P160, K161, E163, L171, N173, G174, A175, N184, T185, I186, H193, K197, K199, N200, R202, N203, I205, S214, E215, H216, D217, G218, D219, S222, 8224, 5232, T233, V235, P236, G237, T238, T239, N240, H249, Q250, P251, V253, T255, D256, E265, R266, T267, E270, R271, F275, V276, R277, F278, L280, L287, L288, D289, 8290, G291, A292, T293, L295, E296, N301, M306, T307, Q308, D309, L311, Q312, Q313, R315, K316, V317, G318, D319, S320, P321, N322, T324, E325, Y326, Y332, 8333, D334, G336, K337, K34I, G342, H351, R353, G354, Q366, G367, T370, V371, G372, 8379, E385, Q388, K389, R392, 5393, E394, P395, R396, P397, G398, V399, L400, L401, R402, P404 and P406 (A1-S45 are located in the Gla domain, the remaining positions are located outside the Gla domain).

The following residues had more than 50% of their side chain exposed to the surface: A1, A3, F4, L5, E6, E7, L8, R9, P10, E14, E16, K18, E19, E20, Q21, S23, E25, E26, E29, K32, A34, E35, R36, K38, L39, I42, S43, G47, D48, A51, S52, S53, Q56, G58, 560, K62, L65, Q66, S67, I69, F71, L73, P74, A75, E77, G78, R79, E82, H84, K85, D86, D87, Q88, L89, I90, V92, N93, E94, G97, T106, G107, T108, K109, S111, E116, S119, L121, A122, D123, G124, V131, E132, L141, E142, K143, R144, N145, A146, S147, K148, P149, Q150, G151, R152, G155, K157, P160, N173, G174, A175, K197, K199, N200, 8202, S214, E215, H216, G218, R224, V235, P236, G237, T238, H249, Q250, V253, D256, T267, F275, R277, F278, L288, D289, R290, G291, A292, T293, L295, N301, M306, Q308, D309, L311, Q312, Q313, R315, K316, G318, D319, N322, E325, D334, K341, G354, G367, V371, E385, K389, R392, E394, R396, P397, G398, R402, P404 and P406 (A1-S43 are located in the Gla domain, the remaining positions are located outside the Gla domain).

Tissue Factor Binding Site

Performing ASA calculations the following residues in human Flat change their ASA in the complex. These residues were defined as constituting the receptor binding site: L13, K18, F31, E35, R36, L39, F40, I42, S43, S60, 1062, D63, Q64, L65, 169, C70, F71, C72, L73, P74, F76, E77, G78, R79, E82, K85, Q88, I90, V92, N93, E94, R271, A274, F275, V276, R277, F278, 8304, L305, M306, T307, Q308, D309, Q312, Q313, E325 and 8379.

Active Site Region

The active site region is defined as any residue having at least one atom within a distance of 10 Å from any atom in the catalytic triad (residues H193, D242, S344): I153, Q167, V168, L169, L170, L171, Q176, L177, C178, G179, G180, T181, V188, V189, 8190, A191, A192, H193, C194, F195, D196, K197, I198, W201, V228, I229, I230, P231, 5232, T233, Y234, V235, P236, G237, T238, T239, N240, H241, D242, I243, A244, L245, L246, V281, S282, G283, W284, G285, Q286, T293, T324, E325, Y326, M327, F328, D338, S339, G340, K341, G342, D343, S344, G345, G346, P347, H348, L358, T359, G360, I361, V362, S363, W364, G365, C368, V376, Y377, T378, R379, V380, Q382, Y383, W386, L387, L400 and F405.

The Ridge of the Active Site Binding Cleft

The ridge of the active site binding cleft region was defined by visual inspection of the FVIIa structure 1FAK.pdb as: N173, A175, K199, N200, N203, D289, R290, G291, A292, P321 and T370.

Example 2

Design of an Expression Cassette for Expression of rhFVII in Mammalian Cells

The DNA sequence shown in SEQ ID NO:1, encompassing the short form of the full length cDNA encoding hFVII with its native short signal peptide (Hagen et al, 1986. PNAS 83:2412), was synthesized in order to facilitate high expression in mammalian cells. First the ATG start codon context was modified according to the Kozak consensus sequence (Kozak, M. *J Mol Biol* 1987 Aug. 20; 196(4):947-50), so that there is a perfect match to the consensus sequence upstream of the ATG start codon. Secondly the open reading frame of the native cDNA was modified by making a bias in the codon usage towards the codons frequently used in highly expressed human genes. Further, two translational stop codons were inserted at the end of the open reading frame in order to facilitate efficient translational stop. The fully synthetic and expression optimized hFVII gene was assembled from 70-mer DNA oligonucleotides and finally amplified using end primers inserting BamHI and HindIII sites at the 5' and 3' ends respectively using standard PCR techniques, which resulted in the following sequence:

```
ggatcccgccaccatggtcagccaggccctccgcctcctgtgcctgctcc
tggggctgcagggctgcctggctgccgtcttcgtcacccaggaggaagcc
catggcgtcctgcatcgccggcgccgggccaatgcctttctggaagagct
ccgcctggctccctggaacgcgaatgcaaagaggaacagtgcagctttg
aggaagcccgggagattttcaaagacgctgagcggaccaaactgttttgg
attagctatagcgatggcgatcagtgcgcctccagcccttgccagaacgg
gggctcctgcaaagaccagetgcagagctatatctgcttctgcctgcctg
cctttgaggggcgcaattgcgaaacccataaggatgaccagctgatttgc
gtcaacgaaaacgggggctgcgagcagtactgcagcgatcacacgggcac
gaagcggagctgccgctgccacgaaggctatagcctcctggctgacgggg
tgtcctgcacgcccacggtggaatacctgcgggaagattcccattctag
aaaagcggaacgctagcaaacccagggccggatcgtcggcgggaaggtc
tgccctaaggggagtgccctggcaggtcctgctcctggtcaacgggc
```

```
                                        -continued
ccagctgtgcggcgggaccctcatcaataccatttgggtcgtgtccgccg ctcactgcttcgataagattaagaattggcggaacctcatcgctgtgctc ggcgaacacgatctgtccgagcatgacggggacgaacagtcccgccggt ggctcaggtcatcattccctccacctatgtgcctggcacgaccaatcacg atatcgctctgctccgcctccaccagcccgtcgtgctcaccgatcacgtc gtgcctctgtgcctgcctgagcggacctttagcgaacgcacgctggcttt cgtccgctttagcctcgtgtccggctggggccagctgctcgaccggggcg ctaccgctctcgagctgatggtgctcaacgtccccggctgatgacccag gactgcctgcagcagtcccgcaaagtgggggactcccccaatatcacgga gtatatgttttgcgctggctatagcgatggctccaaggatagctgcaagg gggactccggcgggcccatgccacgcactatcgcgggacctggtacctc accgggatcgtcagctggggccagggctgcgccacggtggggcactttgg cgtctacacgcgcgtcagccagtacattgagtggctgcagaagctcatgc ggagcgaacccggcccggggtgctcctgcgggcccctttcccttgataa aagctt
```

A vector for the cloning of the generated PCR product encompassing the expression cassette for hFVII was prepared by cloning the intron from pCINeo (Promega). The synthetic intron from pCI-Neo was amplified using standard PCR conditions and the primers:

```
CBProFpr174:
5'- AGCTGGCTAGCCACTGGGCAGGTAAGTATCA -3'
and

CBProFpr175:
5'- TGGCGGGATCCTTAAGAGCTGTAATTGAACT -3'
``` resulting in a 332 by PCR fragment. The fragment was cut with NheI and BamHI before cloning into pcDNA3.1/HygR (obtained from Invitrogen) resulting in PF#34.

The expression cassette for hFVII was cloned between the BamHI and HindIII sites of PF#34, resulting in plasmid PF#226.

Example 3

Expression of Polypeptide Variants in CHO K1 Cells

The cell line CHO K1 (ATCC # CCL-61) is seeded at 50% confluence in T-25 flasks using MEMα, 10% FCS (Gibco/BRL, Cat# 10091), P/S and 5 µg/ml phylloquinone and allowed to grow until confluent. The confluent mono cell layer is transfected with 5 µg of the relevant plasmid described above using the Lipofectamine™ 2000 transfection agent (Life technologies) according to the manufacturer's instructions. Twenty four hours post transfection a sample is drawn and quantified using e.g. an ELISA recognizing the EGF1 domain of hFVII. At this time point relevant selection (e.g. Hygromycin B) may be applied to the cells with the purpose of generating a pool of stable transfectants. When using CHO K1 cells and the Hygromycin B resistance gene as selectable marker on the plasmid, this is usually achieved within one week.

Example 4

Generation of CHO K1 Cells Stably Expressing Polypeptide Variants

A vial of CHO-K1 transfectant pool is thawed and the cells seeded in a 175 cm² tissue flask containing 25 ml of MEMα, 10% FCS, phylloquinone (5 µg/ml), 100 U/l penicillin, 100 µg/l streptomycin and grown for 24 hours. The cells are harvested, diluted and plated in 96 well microtiter plates at a cell density of ½-1 cell/well. After a week of growth, colonies of 20-100 cells are present in the wells and those wells containing only one colony are labelled. After a further two weeks, the media in all wells containing only one Colony is substituted with 200 µl fresh medium. After 24 hours, a medium sample is withdrawn and analysed by e.g. ELISA. High producing clones are selected and used to produce FVII or variant on large scale.

Example 5

Purification of Polypeptide Variants and Subsequent Activation

FVII and FVII variants are purified as follows: The procedure is performed at 4° C. The harvested culture media from large-scale production is ultrafiltered using a Millipore TFF system with 30 KDa cut-off Pellicon membranes. After concentration of the medium, citrate is added to 5 mM and the pH is adjusted to 8.6. If necessary, the conductivity is lowered to below 10 mS/cm. Subsequently, the sample is applied to a Q-sepharose FF column, equilibrated with 50 mM NaCl, 10 mM Tris pH 8.6. After washing the column with 100 mM NaCl, 10 mM Tris to pH 8.6, followed by 150 mM NaCl, 10 mM Tris pH 8.6, FVII is eluted using 10 mM Tris, 25 mM NaCl, 35 mM $CaCl_2$, pH 8.6.

For the second chromatographic step, an affinity column is prepared by coupling of a monoclonal Calcium-dependent antiGla-domain antibody to CNBr-activated Sepharose FF. About 5.5 mg antibody is coupled per ml resin. The column is equilibrated with 10 mM Tris, 100 mM NaCl, 35 mM $CaCl_2$, pH 7.5. NaCl is added to the sample to a concentration of 100 mM NaCl and the pH is adjusted to 7.4-7.6. After 0/N application of the sample, the column is washed with 100 mM NaCl, 35 mM $CaCl_2$, 10 mM Tris pH 7.5, and the FVII protein is eluted with 100 mM NaCl, 50 mM citrate, 75 mM Tris pH 7.5.

For the third chromatographic, the conductivity of the sample is lowered to below 10 mS/cm, if necessary, and the pH is adjusted to 8.6. The sample is then applied to a Q-sepharose column (equilibrated with 50 mM NaCl, 10 mM Tris pH 8.6) at a density around 3-5 mg protein per ml gel to obtain efficient activation. After application, the column is washed with 50 mM NaCl, 10 mM Tris pH 8.6 for about 4 hours with a flow of 3-4 column volumes (cv) per hour. The FVII protein is eluted using a gradient of 0-100% of 500 mM NaCl, 10 mM Tris pH 8.6 over 40 cv. FVII containing fractions are pooled.

For the final chromatographic step, the conductivity is lowered to below 10 mS/cm. Subsequently, the sample is applied to a Q-sepharose column (equilibrated with 140 mM NaCl, 10 mM glycylglycine pH 8.6) at a concentration of 3-5 mg protein per ml gel. The column is then washed with 140 mM NaCl, 10 mM glycylglycine pH 8.6 and FVII is eluted with 140 mM NaCl, 15 mM $CaCl_2$, 10 mM glycylglycine pH 8.6. The eluate is diluted to 10 mM $CaCl_2$ and the pH is adjusted 6.8-7.2. Finally, TWEEN®-80 (polyoxyethylenesorbitan monooleate) is added to 0.01% and the pH is adjusted to 5.5 for storage at −80° C.

The invention claimed is:

1. A conjugate comprising a recombinant Factor VII (FVII) or an activated Factor VII (FVIIa) polypeptide variant consisting of amino acid substitutions P10Q, K32E, T106N, and V253N in SEQ ID NO: 2, wherein the polypeptide variant has at least 10% clotting activity compared to the clotting activity of a wild-type FVII or FVIIa polypeptide, and wherein a sugar moiety is covalently attached to the variant at an N-glycosylation site introduced by the substitution T106N or V253N.

2. The conjugate of claim 1, wherein the variant is in its activated form.

3. The conjugate of claim 1, wherein the conjugate comprises a sugar moiety covalently attached to the variant at each of the two N-glycosylaiton sites introduced by the substitutions T106N and V253N.

4. The conjugate of claim 3, wherein the variant is in its activated form.

5. A method for treating a mammal having a disease or disorder wherein clot formation is desirable, comprising administering to a mammal in need thereof an effective amount of the conjugate of claim 1, wherein said disease or disorder is a bleeding disease or disorder.

6. The method of claim 5, wherein said disease or disorder is hemophilia.

7. The method of claim 5, wherein said disease or disorder is bleeding due to trauma.

8. The method of claim 5, wherein said disease or disorder is a hemorrhage.

9. The method of claim 5, wherein said disease or disorder is uncontrolled bleeding.

10. The method of claim 5, wherein said disease or disorder is thrombocytopenia.

11. A method for treating a mammal having a disease or disorder wherein clot formation is desirable, comprising administering to a mammal in need thereof an effective amount of the conjugate of claim 3, wherein said disease or disorder is a bleeding disease or disorder.

12. The method of claim 11, wherein said disease or disorder is hemophilia.

13. The method of claim 11, wherein said disease or disorder is bleeding due to trauma.

14. The method of claim 11, wherein said disease or disorder is a hemorrhage.

15. The method of claim 11, wherein said disease or disorder is uncontrolled bleeding.

16. The method of claim 11, wherein said disease or disorder is thrombocytopenia.

17. A pharmaceutical composition comprising the conjugate of claim 1 and a pharmaceutically acceptable carrier or excipient.

18. A pharmaceutical composition comprising the conjugate of claim 3 and a pharmaceutically acceptable carrier or excipient.

19. The conjugate of claim 1, wherein the sugar moiety is covalently attached to the variant via the asparagine residue at position 106 or 253 of the amino acid sequence of the variant.

20. The conjugate of claim 3, wherein the sugar moiety is covalently attached to the variant via the asparagine residue at position 106 or 253 of the amino acid sequence of the variant.

21. A conjugate comprising a recombinant Factor VII (FVII) or an activated Factor VII (FVIIa) polypeptide variant consisting of amino acid substitutions P10Q, K32E, T106N, and V253N in SEQ ID NO: 2, wherein the polypeptide variant has at least 10% clotting activity compared to the clotting activity of a wild-type FVII or FVIIa polypeptide, and wherein a sugar moiety is covalently attached to the variant.

\* \* \* \* \*

SEQUENCE LISTING

<160> NUMBER OF SEQ ID NOS: 4

<210> SEQ ID NO 1
<211> LENGTH: 1338
<212> TYPE: DNA
<213> ORGANISM: Homo sapiens
<220> FEATURE:
<221> NAME/KEY: CDS
<222> LOCATION: (115)..(1335)

<400> SEQUENCE: 1

```
atggtcagcc aggccctccg cctcctgtgc ctgctcctgg ggctgcaggg ctgcctggct     60
gccgtcttcg tcacccagga ggaagcccat ggcgtcctgc atcgccggcg ccgg gcc      117
                                                            Ala
                                                             1 aat gcc ttt ctg gaa gag ctc cgc cct ggc tcc ctg gaa cgc gaa tgc     165
Asn Ala Phe Leu Glu Glu Leu Arg Pro Gly Ser Leu Glu Arg Glu Cys
          5                  10                  15 aaa gag gaa cag tgc agc ttt gag gaa gcc cgg gag att ttc aaa gac     213
Lys Glu Glu Gln Cys Ser Phe Glu Glu Ala Arg Glu Ile Phe Lys Asp
         20                  25                  30 gct gag cgg acc aaa ctg ttt tgg att agc tat agc gat ggc gat cag     261
Ala Glu Arg Thr Lys Leu Phe Trp Ile Ser Tyr Ser Asp Gly Asp Gln
     35                  40                  45 tgc gcc tcc agc cct tgc cag aac ggg ggc tcc tgc aaa gac cag ctg     309
Cys Ala Ser Ser Pro Cys Gln Asn Gly Gly Ser Cys Lys Asp Gln Leu
 50                  55                  60                  65 cag agc tat atc tgc ttc tgc ctg cct gcc ttt gag ggg cgc aat tgc     357
Gln Ser Tyr Ile Cys Phe Cys Leu Pro Ala Phe Glu Gly Arg Asn Cys
                 70                  75                  80 gaa acc cat aag gat gac cag ctg att tgc gtc aac gaa aac ggg ggc     405
Glu Thr His Lys Asp Asp Gln Leu Ile Cys Val Asn Glu Asn Gly Gly
             85                  90                  95 tgc gag cag tac tgc agc gat cac acg ggc acg aag cgg agc tgc cgc     453
Cys Glu Gln Tyr Cys Ser Asp His Thr Gly Thr Lys Arg Ser Cys Arg
        100                 105                 110 tgc cac gaa ggc tat agc ctc ctg gct gac ggg gtg tcc tgc acg ccc     501
Cys His Glu Gly Tyr Ser Leu Leu Ala Asp Gly Val Ser Cys Thr Pro
    115                 120                 125 acg gtg gaa tac cct tgc ggg aag att ccc att cta gaa aag cgg aac     549
Thr Val Glu Tyr Pro Cys Gly Lys Ile Pro Ile Leu Glu Lys Arg Asn
130                 135                 140                 145 gct agc aaa ccc cag ggc cgg atc gtc ggc ggg aag gtc tgc cct aag     597
Ala Ser Lys Pro Gln Gly Arg Ile Val Gly Gly Lys Val Cys Pro Lys
                150                 155                 160 ggg gag tgc ccc tgg cag gtc ctg ctc ctg gtc aac ggg gcc cag ctg     645
Gly Glu Cys Pro Trp Gln Val Leu Leu Leu Val Asn Gly Ala Gln Leu
            165                 170                 175 tgc ggc ggg acc ctc atc aat acc att tgg gtc gtg tcc gcc gct cac     693
Cys Gly Gly Thr Leu Ile Asn Thr Ile Trp Val Val Ser Ala Ala His
        180                 185                 190 tgc ttc gat aag att aag aat tgg cgg aac ctc atc gct gtg ctc ggc     741
Cys Phe Asp Lys Ile Lys Asn Trp Arg Asn Leu Ile Ala Val Leu Gly
    195                 200                 205 gaa cac gat ctg tcc gag cat gac ggg gac gaa cag tcc cgc cgg gtg     789
Glu His Asp Leu Ser Glu His Asp Gly Asp Glu Gln Ser Arg Arg Val
210                 215                 220                 225 gct cag gtc atc att ccc tcc acc tat gtg cct ggc acg acc aat cac     837
Ala Gln Val Ile Ile Pro Ser Thr Tyr Val Pro Gly Thr Thr Asn His
                230                 235                 240
```

```
gat atc gct ctg ctc cgc ctc cac cag ccc gtc gtg ctc acc gat cac     885
Asp Ile Ala Leu Leu Arg Leu His Gln Pro Val Val Leu Thr Asp His
        245                 250                 255 gtc gtg cct ctg tgc ctg cct gag cgg acc ttt agc gaa cgc acg ctg     933
Val Val Pro Leu Cys Leu Pro Glu Arg Thr Phe Ser Glu Arg Thr Leu
    260                 265                 270 gct ttc gtc cgc ttt agc ctc gtg tcc ggc tgg ggc cag ctg ctc gac     981
Ala Phe Val Arg Phe Ser Leu Val Ser Gly Trp Gly Gln Leu Leu Asp
275                 280                 285 cgg ggc gct acc gct ctc gag ctg atg gtg ctc aac gtc ccc cgg ctg    1029
Arg Gly Ala Thr Ala Leu Glu Leu Met Val Leu Asn Val Pro Arg Leu
290                 295                 300                 305 atg acc cag gac tgc ctg cag cag tcc cgc aaa gtg ggg gac tcc ccc    1077
Met Thr Gln Asp Cys Leu Gln Gln Ser Arg Lys Val Gly Asp Ser Pro
            310                 315                 320 aat atc acg gag tat atg ttt tgc gct ggc tat agc gat ggc tcc aag    1125
Asn Ile Thr Glu Tyr Met Phe Cys Ala Gly Tyr Ser Asp Gly Ser Lys
        325                 330                 335 gat agc tgc aag ggg gac tcc ggc ggg ccc cat gcc acg cac tat cgc    1173
Asp Ser Cys Lys Gly Asp Ser Gly Gly Pro His Ala Thr His Tyr Arg
    340                 345                 350 ggg acc tgg tac ctc acc ggg atc gtc agc tgg ggc cag ggc tgc gcc    1221
Gly Thr Trp Tyr Leu Thr Gly Ile Val Ser Trp Gly Gln Gly Cys Ala
355                 360                 365 acg gtg ggg cac ttt ggc gtc tac acg cgc gtc agc cag tac att gag    1269
Thr Val Gly His Phe Gly Val Tyr Thr Arg Val Ser Gln Tyr Ile Glu
370                 375                 380                 385 tgg ctg cag aag ctc atg cgg agc gaa ccc cgg ccc ggg gtg ctc ctg    1317
Trp Leu Gln Lys Leu Met Arg Ser Glu Pro Arg Pro Gly Val Leu Leu
            390                 395                 400 cgg gcc cct ttc cct tga taa                                        1338
Arg Ala Pro Phe Pro
            405

<210> SEQ ID NO 2
<211> LENGTH: 406
<212> TYPE: PRT
<213> ORGANISM: Homo sapiens

<400> SEQUENCE: 2

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
            85                  90                  95

Gly Cys Glu Gln Tyr Cys Ser Asp His Thr Gly Thr Lys Arg Ser Cys
        100                 105                 110

Arg Cys His Glu Gly Tyr Ser Leu Leu Ala Asp Gly Val Ser Cys Thr
    115                 120                 125

Pro Thr Val Glu Tyr Pro Cys Gly Lys Ile Pro Ile Leu Glu Lys Arg
130                 135                 140
```

-continued

```
Asn Ala Ser Lys Pro Gln Gly Arg Ile Val Gly Lys Val Cys Pro
145                 150                 155                 160

Lys Gly Glu Cys Pro Trp Gln Val Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405
```

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Primer
    CBProFpr174

<400> SEQUENCE: 3
agctggctag ccactgggca ggtaagtatc a                                    31

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Primer
    CBProFpr175

<400> SEQUENCE: 4
tggcgggatc cttaagagct gtaattgaac t                                    31